United States Patent [19]

Furuoya et al.

[11] Patent Number: 5,079,157
[45] Date of Patent: Jan. 7, 1992

[54] NOVEL CHOLINE OXIDASE AND METHOD FOR PRODUCING THE SAME

[75] Inventors: Itsuo Furuoya, Suita; Takashi Suzuki, Takatsuki; Takeshi Takahashi, Izumi, all of Japan

[73] Assignee: Takeda Chemical Industries, Ltd., Osaka, Japan

[21] Appl. No.: 398,733

[22] Filed: Aug. 25, 1989

[30] Foreign Application Priority Data

Aug. 26, 1988 [JP] Japan .................. 63-212781
Nov. 4, 1988 [JP] Japan .................. 63-280170

[51] Int. Cl.⁵ ................... C12R 1/01; C12Q 1/26
[52] U.S. Cl. ........................ 435/191; 435/25; 435/822
[58] Field of Search .................. 435/191, 822, 25

[56] References Cited

U.S. PATENT DOCUMENTS 4,245,050  1/1981  Nakanishi et al. .............. 435/191

FOREIGN PATENT DOCUMENTS 2751879  11/1977  Fed. Rep. of Germany .
2349599  5/1978  France .

OTHER PUBLICATIONS

"Patent Abst. of Japan", vol. 6, No. 231 (C-135)(1109), Nov. 17, 1982, abstracting JP-A-57-132880.
"Chem. Abst.", 92: col. 92695 (1980), abstracting JP 129187.

*Primary Examiner*—Herbert J. Lilling
*Attorney, Agent, or Firm*—Wenderoth, Lind & Ponack

[57] ABSTRACT

A novel choline oxidase being thermostable at 50° C. at pH 7 to 9 is disclosed. A method for producing the enzyme by using actinomycetes is also disclosed.

2 Claims, 10 Drawing Sheets

NOVEL CHOLINE OXIDASE AND METHOD FOR PRODUCING THE SAME

FIELD OF THE INVENTION

The present invention relates to a novel choline oxidase which is an important enzyme to be used for chemical analyses and clinical tests, and a method for producing the same. The enzyme of the present invention can be widely used. For example, in the field of chemical analyses, it can be used for quantitative determination of choline and, in the field of clinical tests, it can be used for measurement of choline esterase in serum and measurement of phospholipid by using it in combination with phospholipase D.

BACKGROUND OF THE INVENTION

It has been known that choline oxidase (E.C.1.1.3. 17) is produced by bacteria belonging to the genus Arthrobacter (Japanese Patent Publication Nos. 60-4716 and 60-46953), those belonging to the genus Alkaligenes (Japanese Patent Laid Open Publication No. 54-17182), those belonging to the genus Brevibacterium (Japanese Patent Laid Open Publication No. 53-66492), those belonging to the genus Corynebacterium (Japanese Patent Laid Open Publication No. 54-23191), mold fungi belonging to the genus Aspergillus (Japanese Patent Laid Open Publication No. 53-52687), those belonging to the genera Cylindrocarbon, Fusarium and Gibbella (Japanese Patent Laid Open Publication No. 54-35284), those belonging to the genus Penicillium (Japanese Patent Laid Open Publication No. 56-92787), actinomycetes belonging to the genus Streptomyces (Japanese Patent Laid Open Publication No. 57-132880) and the like.

The choline oxidase derived from bacteria belonging to the genus Arthrobacter has a molecular weight of 84,000 and thermostable up to about 40° C. Its optimal reaction temperature is 40° C (Japanese Patent Publication No. 60-4716). The choline oxidase derived from bacteria belonging to the genus Alkaligenes has a molecular weight of 95,000, whose thermal stability is not higher than 37° C. and the optimal reaction temperature is 40° C. (Japanese Patent Laid Open Publication No. 54-17182). The choline oxidase derived from bacteria belonging to the genus Brevibacterium has a molecular weight of 97,000. It is thermostable at 45° C. for 30 minutes and inactivated at 50° C. Its optimal reaction temperature is within the range of from 20° C. to 35° C. (Japanese Patent Laid Open Publication No. 53-66492). The choline oxidase derived from mold fungi belonging to the genus Aspergillus is thermostable up to 35° C. and rapidly inactivated at 40° C. (Japanese Patent Laid Open Publication No. 53-52687). While no description has been found on thermal stability of the enzyme derived from bacteria belonging to the genus Corynebacterium, the optimal reaction temperature is within the range of from 20° C. to 35° C. While no description has been found on the thermal stability of the enzymes derived from mold fungi belonging to the genera Cylindrocarbon, Fusarium and Gibbella, the optimal reaction temperature of those enzymes is 35° C. (Japanese Patent Laid Open Publication No. 54-35284). The enzyme derived from mold fungi belonging to the genus Penicillium is only stable at pH ranging from 7 to 9 at 25° C. for one hour (Japanese Patent Laid Open Publication No. 56-92787). As the microorganism capable of producing the enzyme derived from the genus Streptomyces, only *Streptomyces nigrifaciens* has been known and the enzyme is thermostable up to 30° C. and inactivated at 40° C. Further, the growing temperature of the microorganism is 37° C. or below (Japanese Patent Laid Open Publication No. 57-132880).

These known choline oxidases have molecular weights ranging from 84,000 to 97,000 and are thermostable up to 40° C. or at 45° C. for 30 minutes, but rapidly inactivated at 50° C. The optimal reaction temperatures of all known choline oxidases are 40° C. or below.

Namely, known choline oxidases have a drawback that their thermal stabilities are inferior.

On the other hands, in the case of using an enzyme for clinical tests, chemical analyses and the like, that having higher thermal stability and higher optimal reaction temperature can be used more advantageously. In general, an enzyme has a drawback that it is unstable in comparison with other chemical substances. The principal reason thereof has been considered to be thermal denaturation of an enzyme at a high temperature [Koso Kenkyu-ho (Methods for Studying Enzymes), edited by Shiro AKABORI, Vol. 1, pp. 245 to 246, Asakura Shoten, Japan, 1955]. The "advantageous use" means that an enzyme can be stored for a long period of time in the case of a long-term use, or an enzyme can stand a long-term use in the case of using it repeatedly in an immobilized state. Further, a higher optimal reaction temperature is also advantageous because the enzyme can be used at a higher temperature. In order to obtain choline oxidase which is excellent in thermal stability and has a high optimal reaction temperature, the present inventors have intensively investigated microorganisms capable of producing such enzyme. As the result, it has been found that actinomycetes which can grow at 45° C. or higher produce the desired choline oxidase. Further, the present inventors have isolated and purified the enzyme and studied it to attain the present invention.

OBJECTS OF THE INVENTION

One object of the present invention is to provide a novel choline oxidase having high thermal stability and high optimal reaction temperature.

Another object of the present invention is to provide a method for producing the novel choline oxidase.

These objects as well as other objects and advantages of the present invention will become apparent to those skilled in the art from the following description with reference to the accompanying drawings.

BRIEF EXPLANATION OF THE DRAWINGS

In FIG. 4, the symbol · represents the residual activity of the authentic sample of the enzyme obtained in Example 1, the symbol ○ represents that of the authentic sample obtained in Example 5, the symbol □ represents that of the authentic sample of the enzyme obtained in Example 3, and the symbol Δ represents that of the authentic sample of the enzyme obtained in Example 6. When the four symbols are overlapped in FIG. 4, the symbol · is used.

In FIG. 5, the symbol · represents residual activities of the choline oxidases obtained in Examples 1, 3, 6, 7, 8 and 9 (the six samples showed similar residual activities), and the symbol Δ represents the residual activities of known choline oxidases [choline oxidase derived from bacteria belonging to the genus Alkaligenes (Sigma Chemical Co., U.S.A.), and choline oxidase derived from bacteria belonging to the genus Arthrobacter (Toyo Jozo Co. Ltd., Japan)] (both samples showed similar residual activities).

SUMMARY OF THE INVENTION

Figure 1:
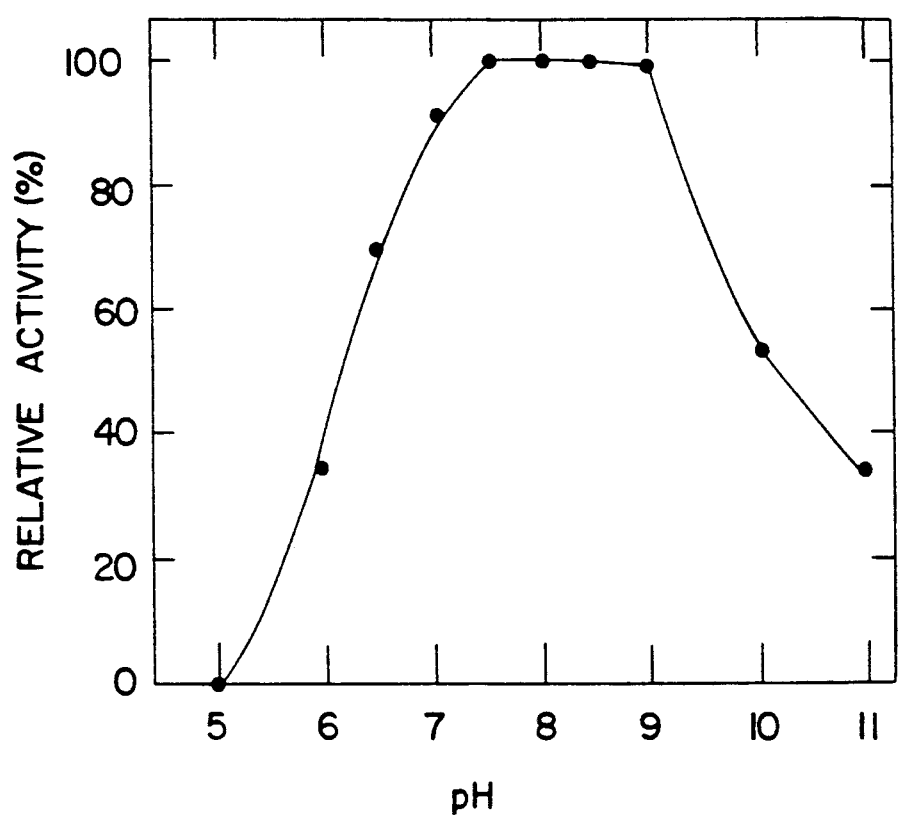
FIG. 1 is a graph illustrating enzyme activity of the choline oxidase obtained in Example 1 hereinafter to choline at various pH's.

According to the present invention, there is provide a method for producing choline oxidase which comprises culturing an actinomycete capable of producing choline oxidase and of growing at a temperature not lower than 45° C. in a culture medium to produce choline oxidase and then recovering the choline oxidase. The present invention also provides a novel choline oxidase having the following physico-chemical properties:

(a) optimal pH: within the range of 7.5 to 9 (Tris-Hcl buffer solution)

(b) stable pH range: 7 to 9 (Tris-HCl buffer solution)

(c) isoelectric point: within the range of 4.5 to 5.5 (electrophoresis using a carrier ampholite)

(d) molecular weight: 50,000 to 95,000 (determined by gel-filtration method using TSK-gel ® ) or $5.5 \times 10^4$ to $6.5 \times 10^4$ (determined by SDS method)

(e) optimal temperature: within the range of about 40° to 55° C. (Tris-HCl buffer solution)

(f) thermostability: stable at 50° C. at pH 7 to 9 (Tris-HCl buffer solution).

DETAILED DESCRIPTION OF THE INVENTION

The actinomycete to be used in the present invention is not limited to a specific strain so far as it is capable of producing choline oxidase and of growing at 45° C. or higher. Examples thereof include those belonging to the genera Streptomyces, Thermoactinomyces and Saccharopolyspora. More specifically, there can be used *Streptomyces thermoluteus* subsp. *fuscus* C-19 (IFO 14770, FERM BP-2007), *Streptomyces thermoluteus* subsp. *fuscus* (IFO 14270), *Streptomyces thermophilus* (IFO 13370), *Thermoactinomyces monosporus* (IFO 14050), *Saccharopolyspora hirsuta* (ATCC 27867), *Saccharopolyspora hirsuta* (ATCC 20501) and *Saccharopolyspora hirsuta* (IFO 13919). The above IFO number means the accession number at the Institute for Fermentation, Osaka (IFO), the FERM BP number means the accession number at Fermentation Research Institute, Agency of Industrial Science and Technology, Ministry of International Trade and Industry (FRI) and the ATCC number means the accession number at the American Type Culture collection, respectively. *Streptomyces thermoluteus* subsp. *fuscus* C-19 has been deposited at IFO since July 25, 1988 and at FRI since Aug. 20, 1988 under the Budapest Treaty, respectively. The other strains are known strains listed on "List of Cultures" 18th edition, Vol. 1, (1988) published by IFO or "Catalogue of Bacteria, Pharges and rDNA Vectors" 16th edition (1985) published by ATCC.

Mycological properties of *Streptomyces thermoluteus* subsp. *fuscus* C-19 strain are as follows:

(A) Morphology

Under observation with naked eyes, the aerial hyphae forming the spores are colored in grege citron gray (lfe) and the vegetative hyphae are colored in golden olive (11/21 g) according to the color indicated by "Color Harmony Manual".

While any soluble pigment is usually not produced, a pigment of light antique gold (11/2 ic) according to the color indicated by "Color Harmony Manual" is rarely produced.

Microscopic observation of the culture on starch inorganic salt agar medium at 37° C. for 10 to 15 days is as follows:

The aerial hyphae are of 0.8 to 1.2 μmin diameter and straight or curly or wavy, and they elongate with simple branching, and form a chain of a number of spores. The chain of spores is wavy or straight [rectus-flexibilis (RF)], while sometimes curly or loop [rectinaculum-apertum (RA)], rarely spiral wound once or twice. The spores are elliptical, sometimes spherical, the size of which ranges from 0.8–1.2 μm to 1.0–1.8 μm, and the surface of which is smooth. The vegetative hyphae are simply branched, extended wavy or curly, whose diameter ranges from 0.6 to 0.8 μm, and no fission of hyDhae nor spore is observed. No adherent flagellospore and sporangium are observed.

(B) Cell components

The strain was cultured with shaking in a starch-inorganic salt medium for 24 hours and cells were collected. By using the whole cells thus collected, diaminopimelic acid was analyzed according to the method described by Becker et al. [Applied Microbiology, Vol. 12 (5) pp 421–423, 1964]. As the result, L,L-diaminopimelic acid was detected, but no meso-type was detected.

Samples of the same cells were subjected to analysis of reducing sugars of the cell walls according to the method described by Lechevalier and Lechevalier (International Journal of Systematic Bacteriology, Vol. 20, pp 435–443, 1970). Detection of reducing sugars was conducted by, in addition to the conventional filter paper chromatography, liquid chromatography. The liquid chromatography was carried out by employing a high performance liquid chromatography apparatus (LC-5A type) and a fluorophotometer (RT-530) according to the method for analysis of reducing sugars by means of liquid chromatography described in "Bunseki Kagaku (Analytical Chemistry)", Vol. 32, pp E207 to E210. As the result, ribose, glucose and galactose were detected.

(C) Cultural characteristics

The strain were culture by using the following culture media and incubating at 37° C. for 21 days. The characteristics observed were as follows. Indication of color tone was made according to "Color Harmony Manual".

(C-1) Sucrose nitrate agar medium

Growth: moderate, white (a)
Aerial hyphae: moderate, white (a)
Soluble pigment: no production (C-2) Glucose asparagine agar medium Growth: good, white (a)
Aerial hyphae: good, white (a)
Soluble pigment: golden brown (3 pg)

(C-3) Glycerol asparagine agar medium

Growth: moderate, white (a)
Aerial hyphae: moderate, white (a)
Soluble pigment: no production (C-4) Starch agar medium Growth: very good, grege citron gray (1 fe)
Aerial hyphae: very good, white or cobalt grey (2 fe)
Soluble pigment: light antique gold (11/2 ic)

(C-5) Tyrosine agar medium

Growth: good, cobalt gray (2 fe)
Aerial hyphae: white (a) or grege citron grey (1 fe)
Soluble pigment: topaz butter scotch (3 ne)

(C-6) Nutrient agar medium

Growth: moderate, cobalt gray (2 fe)
Aerial hyphae: moderate, white (a) or cobalt gray (2fe)
Soluble pigment: no production (C-7) Yeast malt agar medium Growth: good, cobalt grey (2 fe)
Aerial hyphae: good, white (a) or grege citron grey (1 fe)
Soluble pigment: no production
Growth: very good, olive grey (1 ih)
Aerial hyphae: very good, white (a) or dark cobalt grey (2 ih)
Soluble pigment: mustard old gold (2 le)

(D) Physiological properties (D-1) Production of melanoid pigment

Negative on tryptone yeast agar medium, and positive on both tyrosine agar medium and peptone yeast iron agar medium.

(D-2) Liquefaction of gelatin

Positive on glucose peptone gelatin agar medium.

(D-3) Hydrolysis of starch

Positive on starch inorganic salt agar medium.

(D-4) Skimmed mild medium:

No coagulation, but peptonization.

(D-5) Assimilation of carbon sources

Positive : L-arabinose, glycerol, D-xylose, D-galactose, D-fructose, L-rhamnose, inositol, D-mannitol, sucrose, D-raffinose, salicin and D-glucose.

Negative : D-arabinose, L-xylose, L-sorbose, D-sorbitol, xylitol, D-fucose and D-tagatose.

(D-6) Growing temperature

Growing temperature on starch agar medium is 17° to 51° C.

As described hereinabove, the sample strain (C-19) produces aerial hyphae having a chain of many spores from the vegetative hyphae which do not occur fission, contains L,L-diaminopimelic acid in the cell wall and contains, as the constituent sugars, ribose, glucose and galactose. Therefore, the strain is recognized as that belonging to the genus Streptomyces. The diameter of hyphae and the size of spores are recognized to be typical as those of the genus Streptomyces.

One of the characteristic properties of the sample strain is its growing temperature of not lower than 50° C. According to the definition described in "Development in Industrial Microbiology", Vol. 23, pp 61–78 (1982), this can be classified into *Thermophilic Actinomyces*. And, the chain of spores is wavy or straight (RF), sometimes, loop-like or curly (RA) and, rarely, spiral wound once or twice. The surface of each spore is smooth and a soluble pigment is sometimes produced. Melanoid pigment is produced on tyrosine agar medium and peptone yeast iron agar medium. Other characteristic properties of the sample strain is that the nitrate reduction test is negative and that the assimilability of carbon sources covers a relatively broad range. Strains of the genus Streptomyces having these characteristics have been investigated with reference to "Development Industrial Microbiology", Vol. 23, pp 61–78 (1982), "Bergey's Manual of Determinative Bacteriology", 8th Ed. pp 750–828, and "International Journal of Systematic Bacteriology", Vol. 18, pp 69–189, and it has been found that strains belonging to *Streptomyces eurythermus* are analogous ones. On the other hand, *Streptomyces thermoluteus subsp. fuscus* described in "Acta Microbilogica Sinica", Vol. 21, p 414 (1981) can also be recognized as an analogous strain.

Further, the following the thermophilic and thermostable strains belonging to the genus Streptomyces which were deposited at the Institute for Fermentation, Osaka were selected and compared with the sample strain.

*Streptomyces thermovulgaris* IFO 1238 and 13089
*Streptomyces thermoviolaceus* IFO 13473, 13905, 12382 and 13387
*Streptomyces thermodiastaticus* IFO 13468
*Streptomyces thermophilus* IFO 12381 and 13370
*Streptomyces thermostable* IFO 13088
*Streptomyces thermolilacinus* IFO 14274
*Streptomyces thermoluteus* IFO 14269
*Streptomyces thermoluteus subsp. fuscus* IFO 14270
*Streptomyces thermoatroviridis* IFO 14276
*Streptomyces thermocastaneus* IFO 14275
*Streptomyces thermocoerulecens* IFO 14273
*Streptomyces thermocyaneomaculatus* IFO 14272
*Streptomyces thermocycineovilaceus* IFO 14271
*Streptomyces macrosporus* IFO 14748 14750
*Streptomyces megasporus* IFO 14749
*Streptomyces macrosporeus* IFO 1279
*Streptomyces eurythermus* IFO 12764, and

*Streptomyces fradiae* IFO 3718.

Namely, the sample strain (C-19) and the above strains deposited at IFO were planted on glucose asparagine agar medium, starch agar medium and yeast malt agar medium by smearing pores on the surface of agar plates, incubated at temperatures of 28° C., 37° C. and 45° C. for 21 days, respectively. Colors of the hyphae and pores grown during this period were observed and compared each other. As the strains showing colors similar to those of the sample strains, *Streptomyces eurythermus* IFO 12764 and *Streptomyces thermoluteus subsp. fuscus* IFO 14270 were selected and these two strains were further compared with the sample strain in detail.

As shown in Table 1, it has been recognized that these three strains including the sample strain completely agree with each other in view of growth and the color of aerial hyphae on the glucose asparagine agar medium and starch agar medium. And, the branching form of hyphae and the form of vegetative hyphae of these strains almost agree with each other. The surface structures of spores of three strains are in complete agreement with each other and the sizes of spores agrees with each other. Regarding the production of soluble pigments on the agar media, some differences are observed among these three strains. Regarding the formation of soluble pigment on glucose asparagine agar medium, IFO 14270 does not produce the pigment and the other two strains produce the pigment. Among these three strains, there are observed some differences in the properties regarding the growth, the aerial hyphae and the soluble pigment on yeast malt agar medium.

Among these three strains, no substantial difference is observed in the growing temperature. These three strains are in complete agreement with each other in view of gelatin liquefaction, starch hydrolysis, properties in skimmed milk medium and the production of melanoid pigment and nitrate reduction in tyrosine agar medium, peptone yeast iron agar medium and tryptone yeast agar medium.

The sample strain and IFO 14270 are in complete agreement with each other in assimilation of carbon sources tested with respect to L-arabinose, D-xylose, D-glucose, D-fructose, sucrose, inositol, L-rhamnose, D-raffinose and D-mannitol. IFO 12764 substantially agrees with the other two strains in assimilation of almost all carbon sources, but shows different results in inositol and L-rhamnose. That is, IFO 12764 does not show assimilation with these carbon sources, but the other two strains show such assimilation. The sample strain and IFO 14270 produce choline oxidase, but IFO 12764 does not produce it.

These three strains are considered to have good resemblance to each other in view of morphology, growth conditions and properties. However, some differences are observed among them in view of physiological properties. That is, the sample strain completely agrees with IFO 14270 with respect to all the items tested, while it is different from IFO 12746 in assimilation of inositol and L-rhamnose and in the production of choline oxidase.

Based on these characteristics, the sample strain C-19 is considered to be very similar to IFO 12764 and IFO 14270 and, particularly, in view of the results of the above physiological properties, it has close resemblance to IFO 14270. Therefore, it is reasonable to identify the sample strain as *Streptomyces thermoluteus subs. fuscus*. Thus, the sample strain has been named as *Streptomyces thermoluteus subsp. fuscus* C-19.

TABLE 1

| | Sample strain C-19 | St. eurythermus IFO 121764 | St. thermoluteus subsp. fuscus IFO 14270 |
|---|---|---|---|
| (1) Microscopic observation | | | |
| Aerial hyphae form | straight, curly or wavy, elongation with simple blanching chain of spores | the same as the sample strain C-19 | the same as the sample strain C-19 |
| Aerial hyphae diameter ($\mu$m) | 0.8-1.2 | 1.0-1.4 | 0.8-1.2 |
| Shape of spores | chain of spores being straight, wavy (RF) or curly, loop (RA), rarely spiral wound once or twice; spores being spherical or elliptical | the same as the sample strain C-19 | the same as the sample strain C-19 |
| Size of spores ($\mu$m) | 0.8-1.2, 1.0-1.8 | 1.0-1.4, 1.2-1.8 | 1.0-1.5, 1.2-1.7 |
| Surface structure of spores | smooth | smooth | smooth |
| Vegetative hyphae form | straight, wavy or curly, elongation with simple blanching | the same as the sample strain C-19 | the same as the sample strain C-19 |
| Vegetative hyphae diameter ($\mu$m) | 0.6-0.8 | 0.6-0.8 | 0.6-0.8 |
| (2) Growth state, color | | | |
| Glucose asparagine medium | | | |
| Growth | good, white (a) | good, white (a) | good, white (a) |
| Aerial hyphae | good, white (a) | good, white (a) | good, white (a) |
| Soluble pigment | golden blown, (3 pg) | golden blown, cigaret blown (3 pi) | no production |
| Starch agar medium | | | |
| Growth | good, grege citron gray (1 fe) | good, grege citron gray (1 fe) | good, grege citron gray (1 fe) |
| Aerial hyphae | good, white (a) or petty grege (1 dc) | good, white (a) or petty grege (1 dc) | good, white (a) or petty grege (1 dc) |
| Soluble pigment | light antique gold (11/2 ic) | no production | cream (11/2 ca) |
| Yeast malt agar medium | | | |
| Growth | good, cobalt gray | good, grege citron | good, ivory tint (2 cb) |

TABLE 1-continued

|  | Sample strain C-19 | *St. eurythermus* IFO 121764 | *St. thermoluteus* subsp. fuscus IFO 14270 |
| --- | --- | --- | --- |
| Aerial hyphae | (2 fe) good, white (a) or grege citron gray (1 fe) | gray (1 fe) good, white (a) or petty grege (1 dc) | good, white (a) or parchment (1 cb) |
| Soluble pigment | no production | dark luggage tan (4 pg) | antique gold (11/2 me) |
| (3) Physical properties | | | |
| Growing temperature range (°C.) | 17–51 | 15–51 | 17–49 |
| Gelatin liquefaction | + | + | + |
| Starch hydrolysis | + | + | + |
| Skimmed milk medium | no coagulation, but peptonization | no coagulation, but peptonization | no coagulation, but peptonization |
| Melanoid pigment production | | | |
| Tyrosine agar medium | + | + | + |
| Peptone yeast iron agar medium | + | + | + |
| Tryptone yeast agar medium | − | − | − |
| Reduction of nitrate | − | − | − |
| Carbon source assimilation | | | |
| L-Arabinose | + | + | + |
| D-Xylose | + | + | + |
| D-Glucose | + | + | + |
| D-Fructose | + | + | + |
| Sucrose | + | + | + |
| Inositol | + | − | + |
| L-rhamnose | + | − | + |
| D-Raffinose | + | + | + |
| D-Mannitol | + | + | + |
| Choline oxidase production | + | − | + |

In order to accumulated thermostable choline oxidase by culturing the above actinomycete according to the method of the present invention, conventional stationary culture, shaking culture, submerged culture or solid culture can be employed. Particularly, submerged culture is preferred. As the culture medium, any medium having a conventional composition can be used so far as the microorganism to be used can grow thereon. As the assimilable carbon source, there can be used suitable materials selected from carbohydrates (e.g., glucose, lactose, maltose, sucrose, etc.), fats and oils (e.g., soybean oil, corn oil, etc.), fatty acids (e.g., stearic acid, etc.), organic acids (e.g., succinic acid, lactic acid, acetic acid, etc.), alcohols (e.g., glycerine, ethylene glycol, ethanol, etc.) and the like. They can be used alone or in combination thereof. As the nitrogen source, there can be used organic nitrogen sources, for example, peptone, soybean powder, cotton seed powder, corn steep liquor, yeast extract, meat extract, whey, casein and the like as well as inorganic nitrogen sources, for example, ammonium sulfate, ammonium chloride, ammonium nitrate, ammonium phosphate and the like at need. They can be used alone or in combination thereof. In addition to the carbon source and nitrogen sources, it is preferred to add other factors which are required for or enhances growth and enzyme production such as minerals, amino acids and vitamines to the culture medium. Further, in order to induce thermostable choline oxidase, choline or a choline derivative can be added as an inducing factor. For the purpose of controlling pH and foaming during culturing, it is advantageous to add a caustic alkali solution, sodium carbonate, calcium salts such as calcium carbonate and an antifoaming agent.

The incubation temperature can be appropriately chosen according to the growing temperature of a particular microorganism to be used. Usually, it is advantageous to conduct incubation at 15° C. to 70° C., preferably, 25° C. to 60° C. And, the incubation is carried out for a period of time sufficient for the growth of a particular microorganism to be used and for the production of thermostable choline oxidase, usually, for one day to seven days.

By culturing in this way, usually, thermostable choline oxidase is accumulated in the cells of the microorganism. Then, the living cells are collected from a culture broth by, for example, centrifugation, precipitation, aggregation or filtration with a porous membrane, high polymer membrane, ceramic membrane or the like. The cells thus collected are disrupted by, for example, freezing-thawing treatment, grinding, ultrasonic treatment, pressure shearing, osmotic pressure, dissolution of cell walls, treatment with a surfactant or a combination of these means to solubilize the enzyme. Then, the resulting crude enzyme solution is subjected to conventional means for purification of enzymes such as protamine treatment, salting out, treatment with an organic solvent, treatment with a surfactant, isoelectric precipitation, electrophoresis, ion-exchange chromatography, hydrophobic chromatography, gel-filtration, affinity chromatography, crystallization or a combination of these means to obtain an authentic sample of the desired enzyme which is a single homogeneous protein.

Enzymological and physico-chemical properties of the choline oxidase thus obtained are as follows.

(1) Activity

The enzyme oxidizes choline to give betaine aldehyde, and oxidizes betaine aldehyde to give betaine. In the case of oxidation of choline, one mole of choline produces one mole of betaine aldehyde and one mole of hydrogen peroxide and, further, one mole of betaine aldehyde produces one mole of betaine and one mole of hydrogen peroxide. That is, one mole of choline produces one mole of betaine and two moles of hydrogen peroxide. And, in the case of oxidation of betaine aldehyde, one mole of betaine aldehyde produces one mole of betaine and one mole of hydrogen peroxide.

(2) Method of determining enzymatic activity 2.1% Choline chloride solution (97 ml) prepared by dissolving choline chloride (2.1 g) in 100 ml of a 0.1 M Tris-HCl buffer solution (pH 8.0), aqueous 1.0% 4-aminoantipyrine solution (1.0 ml) and aqueous 1.5% phenol solution (2.1 ml) are mixed. A peroxidase (obtained from horse radish, 100 units/mg, Type I, Sigma Chemical Co., U.S.A.) is dissolved in the above mixture to obtain a reaction mixture. The reaction mixture (3.0 ml) is placed in a cuvette (d = 1.0 cm) and subjected to pre-heating at 37° C. for 5 minutes. Then, the changes of absorbance at 500 nm at 37° C. are recorded by an autographic recording spectrophotometer (UV-260 Type, Shimadzu Seisakusho, Ltd.) and the changes of absorbance per minute ($\Delta A/min.$) from the initial straight line portion are determined. The enzymatic activity is calculated by the following formula:

Enzymatic activity
$(U/ml) = \Delta A/min. \times 10.17 \times \text{dilution ratio}$ (3) Substrate specificity According to the above determination method of enzymatic activity, various substrates shown in Table 2 were used in place of choline chloride in the reaction mixture, their relative activities to choline were determined. As the enzyme, the authentic sample obtained in Example 1 hereinafter was employed.

TABLE 2

| Substrate | Relative activity (%) |
|---|---|
| Choline | 100 |
| Betaine aldehyde | 41.9 |
| N-methylaminoethanol | 0 |
| Dimethylaminoethanol | 10 |
| Monoethanolamine | 0 |
| Diethanolamine | 0 |
| Triethanolamine | 0 |

As is clear from Table 2, the enzyme of the present invention shows high activities against choline and betaine aldehyde.

(4) Optimal pH

Enzymatic activities of the choline oxidase obtained in Example 1 to choline were determined by using citric acid-dipotassium hydrogen phosphate buffer solution (pH 4 to 7), phosphoric acid-potassium hydroxide buffer solution (pH 6 to 8), Tris-HCl buffer solution (pH 7 to 9) and glycine-sodium hydroxide (pH 9 to 11).

The results are shown in FIG. 1.

As shown in FIG. 1, the optimal pH is within the range from 7.5 to 9.

(5) pH stability

The choline oxidase obtained in Example 1 (50 l, concentration: 8 U/ ml) was added to citric acid-dipotassium hydrogen phosphate buffer solution buffer solution (pH 4 to 7), phosphoric acid-potassium hydroxide buffer solution (pH 6 to 8), Tris-HCl buffer solution (pH 7 to 9) or glycine-sodium hydroxide (pH 9 to 11) (1.2 ml) and the mixture was allowed to stand at 37° C. for 2 hours. Then, 0.5 M Tris-HCl buffer solution (pH 8.0) (0.5 ml) was added to the mixture to adjust pH. The residual activities were determined by the above method for calculating enzymatic activities.

Figure 2:
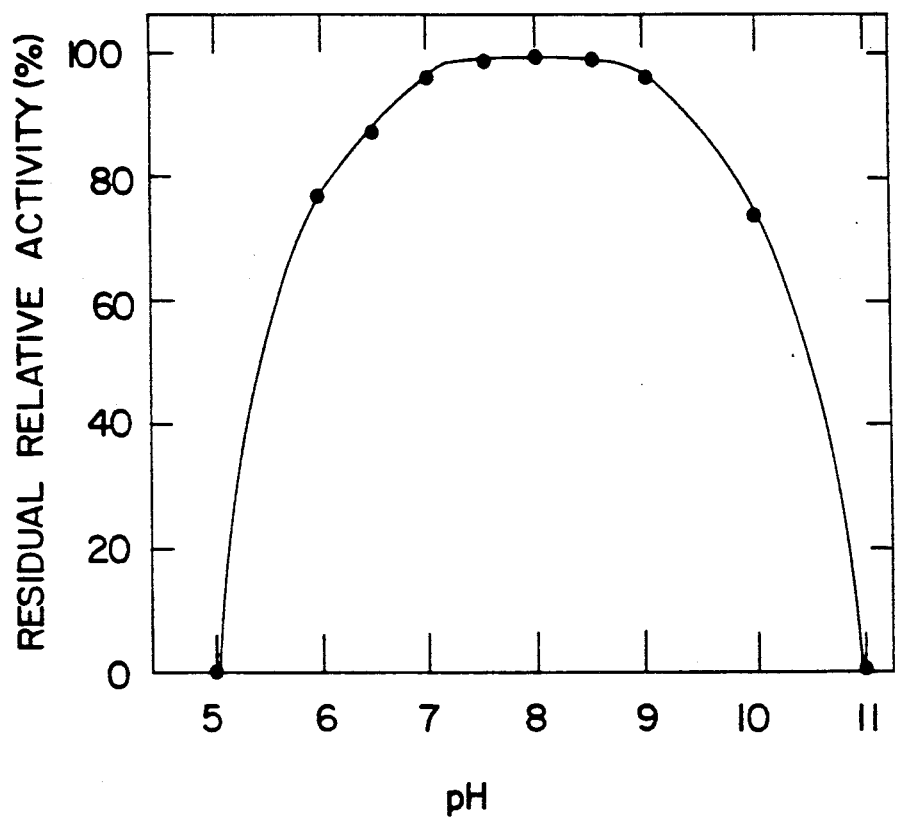
FIG. 2 is a graph illustrating residual activity of the choline oxidase obtained in Example 1 at various pH's.

The results are shown in FIG. 2.

As is clear from FIG. 2, the enzyme of the present invention is stable at about pH 7 to 9.

(6) Optimal temperature

Enzymatic activities of the authentic sample of the purified enzyme obtained in Example 1 were determined at various temperatures.

Figure 3:
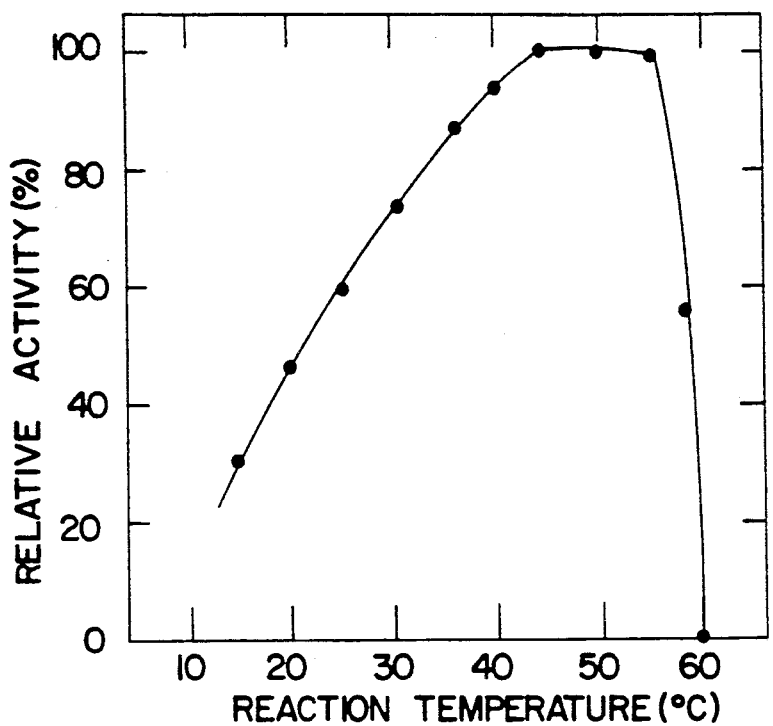
FIG. 3 is a graph illustrating enzyme activity of the choline oxidase obtained in Example 1 at various temperatures.

The results are shown in FIG. 3.

As seen from FIG. 3, the optimal temperature of the enzyme of the present invention is recognized to be within the range of 45° to 55° C.

(7) Thermal stability 0.05M Tris-HCl buffer solution (pH 7.5) containing choline oxidase (0.5 U/ml) obtained in Example 1, 3, 5 or 6, was heated at each temperature for 15 minutes and the residual enzymatic activities were determined.

Figure 4:
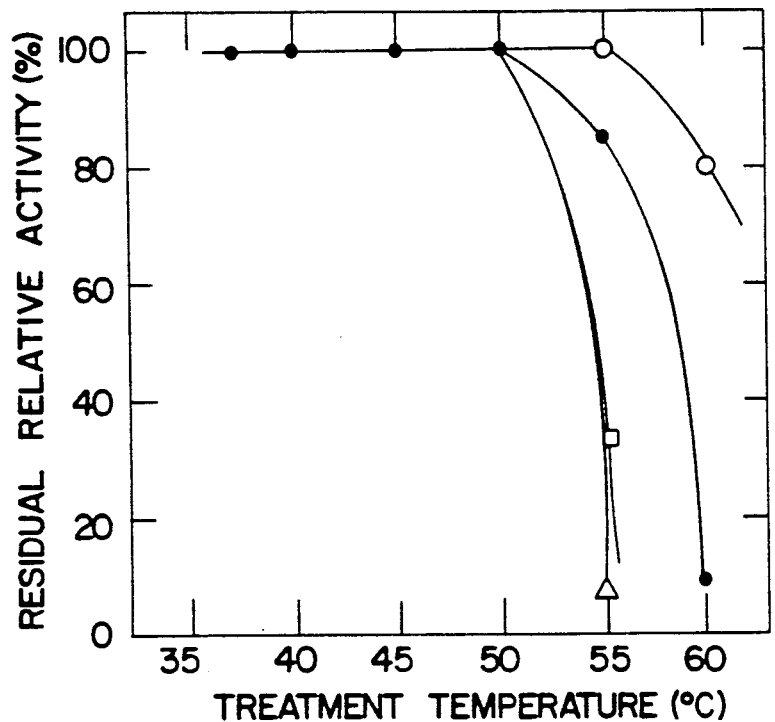
FIG. 4 is a graph illustrating residual activities of the choline oxidases obtained in Examples 1, 3, 5 and 6 hereinafter, after heating for 15 minutes at various temperatures.

The results are shown in FIG. 4. It is apparent that the enzyme of the present invention is stable at temperature, not lower than 50° C.

Then, authentic samples of choline oxidase of the present invention obtained in Examples 1, 3, 5 and 6 (0.5 U/ml, 0.05M Tris-HCl buffer solution, pH 7.5) and commercially available authentic samples of enzyme (choline oxidase obtained from bacteria belonging to the genus Alkaligenes, manufactured by Sigma Chemical Co., U.S.A., and choline oxidase obtained from bacteria belonging to the genus Arthrobacter, manufactured by Toyo Jozo Co., Ltd., Japan) (0.5 U/ml, 0.05M Tris-HCl buffer solution, pH 7.5) were subjected to heat treatment of 50° C for two hours to determine their thermal stabilities.

Figure 5:
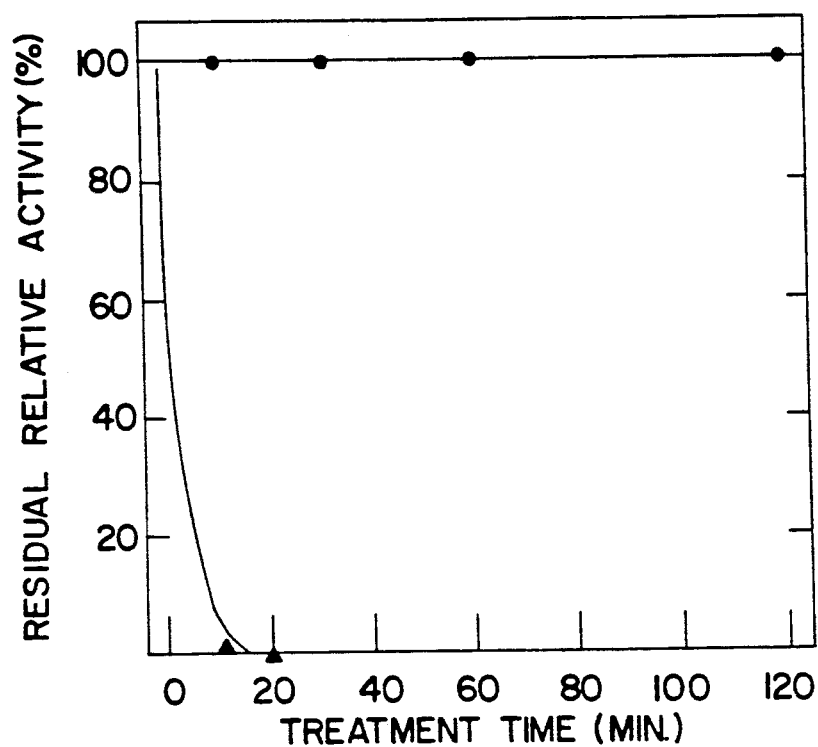
FIG. 5 is a graph illustrating thermal stability at 50° C. on treatment for various period of times.

The results are shown in FIG. 5. The choline oxidase of the present invention is stable at 50° C., while the conventional choline oxidase is quickly inactivated at 50° C.

(8) Inhibitors

Various substances were added to the reaction mixture to be used for the determination of enzymatic activity as described in the above (2) and the inhibitory effects were examined.

The results were shown in Table 3.

TABLE 3

| Additive | Concentration | Relative Activity (%) |
|---|---|---|
| $CaCl_2$ | 5 mM | 100 |
| $MgCl_2$ | 5 mM | 93.8 |
| $BaCl_2$ | 5 mM | 100 |
| $ZnCl_2$ | 5 mM | 82.9 |
| $MnCl_2$ | 5 mM | 100 |
| $CoCl_2$ | 5 mM | 36.9 |
| KCl | 5 mM | 98.0 |
| NaCl | 5 mM | 100 |
| $NH_4Cl$ | 5 mM | 100 |
| LiCl | 5 mM | 100 |
| $MoCl_5$ | 1.0 mM | 18.1 |
| $HgCl_2$ | 0.05 mM | 83.3 |
|  | 0.5 mM | 60.1 |
|  | 1.0 mM | 50.0 |
| Without addition | — | 100 |

(9) Measurement of molecular weight

The molecular weight of the authentic sample of choline oxidase obtained in Example 1 was determined by the following method.

(a) The molecular weight of the enzyme was determined by molecular sieve high performance liquid chromatography under the following conditions:

column: TSK gel ® G 3000 SW (inner diameter: 7.5 mm ×60 cm, Toso, Ltd., Japan)

apparatus: high performance liquid chromatography apparatus (Computer Control Excellent Pump CCPE type, UV detector: UV-8000 type) manufactured by Toso, Ltd., Japan developing agents: 50 mM potassium sodium phosphate buffer solution (pH 7.0) and 0.2M NaCl flow rate: 0.5 ml/min. [see "High Performance Liquid Chromatography of Proteins Peptides", pp 203–213 ("Kagaku" extra number 102, 1984)]. The retention time of the sample was 41.4 minutes. As the standard samples, yeast glutamate dehyrogenase (molecular weight: 290 K), swine cardiac muscle lactate dehydrogenase (molecular weight: 142K), yeast enolase (molecular weight: 67K), yeast adenylate kinase (molecular weight: 12.4K) and equine cardiac muscle cytochrome C (molecular weight: 12.4K) were used. The molecular weight of the enzyme of the present invention was about 54000.

(b) The molecular weight of the enzyme was determined by gel-filtration of protein denatured by treatment with guanidine hydrochloride under the following conditions:

column: TSK gel ® G 2000 SW x L (inner diameter 7.8 mm ×30 cm)

apparatus: the same as that used in the above (a)

developing agent: 6N guanidine hydrochloride, 1 mM EDTA-2Na and 10 mM phosphate buffer solution (pH 6.5) as developing agents flow rate: 0.3 ml/min. [see "High Performance Liquid Chromatography of Proteins Peptides", pp 241–251 ("Kagaku" extra number 102, 1984)]. The retention time of the sample was 23.8 minutes and the molecular weight was about 60000.

(c) The molecular weight of the enzyme of the present invention was determined according to polyacrylamide electrophoresis using a discontinuous buffer solutions system described in "Nature", Vol. 227, p 680 (1970). The sample was treated in a solution containing a 0.0625 M Tris-HCl buffer solution (pH 6.8), 2% SDS, 10% glycerol and 5% mercaptoethanol at 100° C. for 5 minutes. Then, electrophoresis was conducted by using SDS-PAG plate 10/20 (84×90×1.0 mm, manufactured by Daiichi Kagaku Yakuhin Ltd., Japan) and a solution containing 0.025 M Tris, 0.1% SDS and 0.192 M glycine as the electrophoresis buffer solution (pH 8.4) under conditions of the current of 60 mA for 60 minutes. As the standard samples, phosphorylase b (molecular weight: 94000), bovine serum albumin (molecular weigh: 67000), ovalbumin (molecular weight: 43000), carbonic anhydrase (molecular weight 30000), trypsin inhibitor (molecular weight: 20100) and α-lactalbumin (molecular weight: 14400) were used. The molecular weight of the enzyme of the present invention was determined to be about 64,000.

(10) Isoelectric point

Isoelectric electrophoresis was conducted by using amphorine polyacrylamide gel plate (pH 4.0 to 6.5, manufactured by LKB Co.). The isoelectric point was about 4.5.

(11) Electrophoresis

Figure 6:
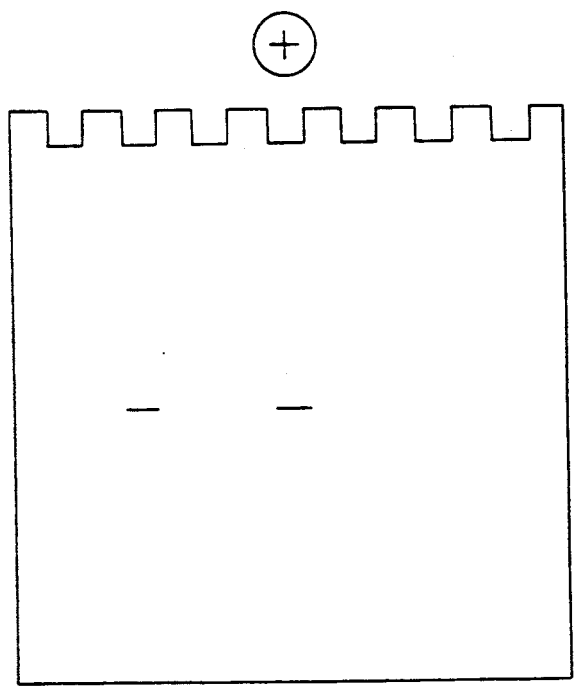
FIG. 6 is a chart illustrating the pattern of concentration gradient polyacrylamide electrophoresis of choline oxidase obtained in Example 1.

The choline oxidase obtained in Example 1 was treated with a solution composed of a 0.0625 M Tris-HCl buffer solution (pH 6.8) and 15% glycerol and subjected to electrophoresis by using a concentration gradient acrylamide gel, PAG plate 4/15 (84×90×1.0 mm, Daiichi Kagaku Yakuhin, Ltd., Japan) and a solution (pH 8.4) composed of 0.025 M Tris and 0.192 M glycine as the buffer solution for electrophoresis under conditions of a current of 30 mA for 60 minutes. As shown in FIG. 6, the protein tested showed a single band at 42 mm from the positional terminal.

(12) Absorption spectrum

The authentic sample of choline oxidase obtained in Example 1 was dissolved in 0.05 M Tris-HCl buffer solution (pH 8.0) so that the concentration thereof became 0.25 mg/ ml or 10 mg/ ml and the absorption spectrum of the resulting solution was determined by an autographic recording spectrophotometer (UV-260 Type, Shimadzu Seisakusho, Ltd., Japan).

Figure 7:
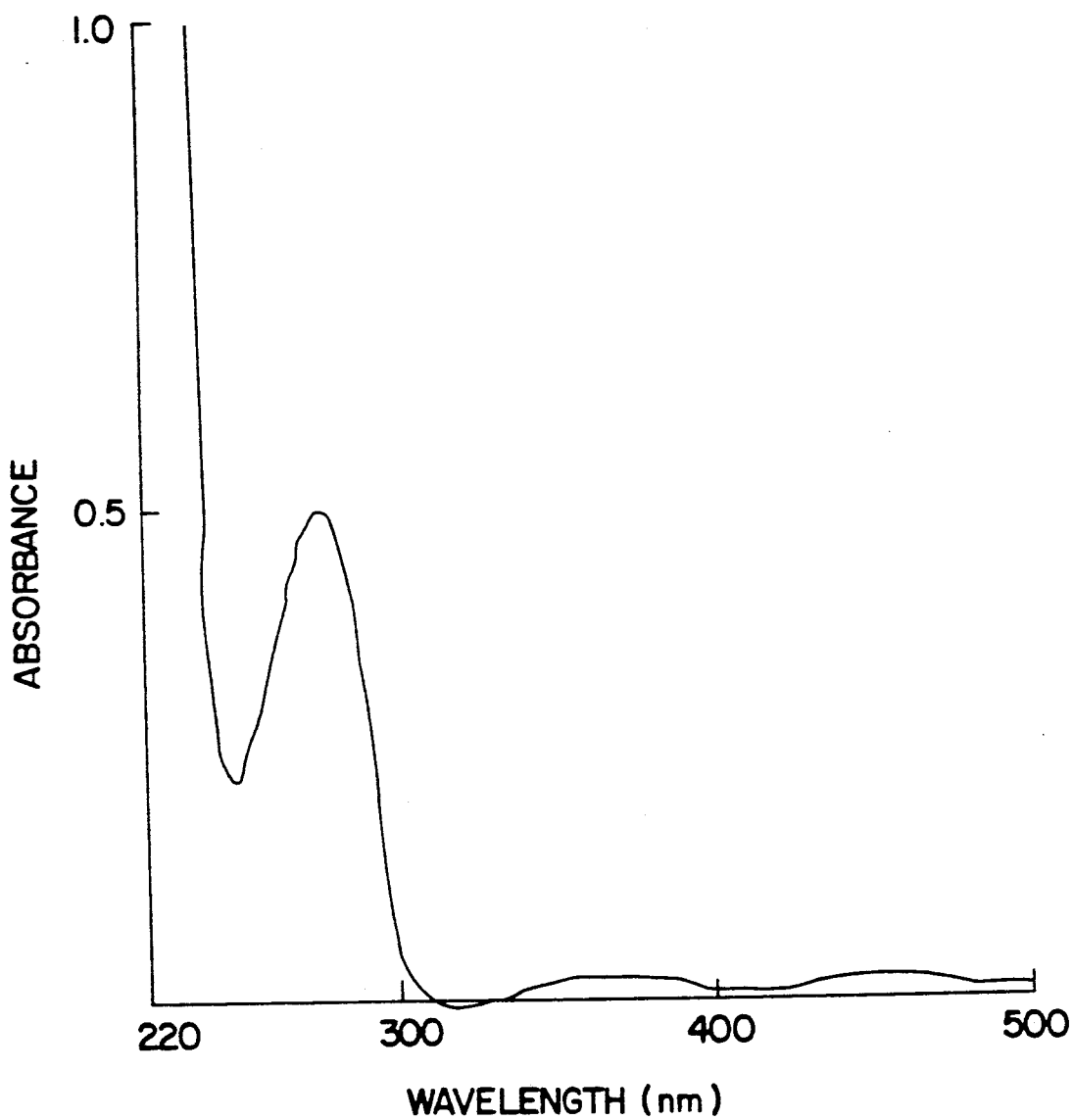
FIG. 7 is an absorption spectrum of the authentic sample of the enzyme obtained in Example 1 (0.25 mg/ml, 0.05M Tris-HCl buffer solution, pH 8.0).
Figure 8:
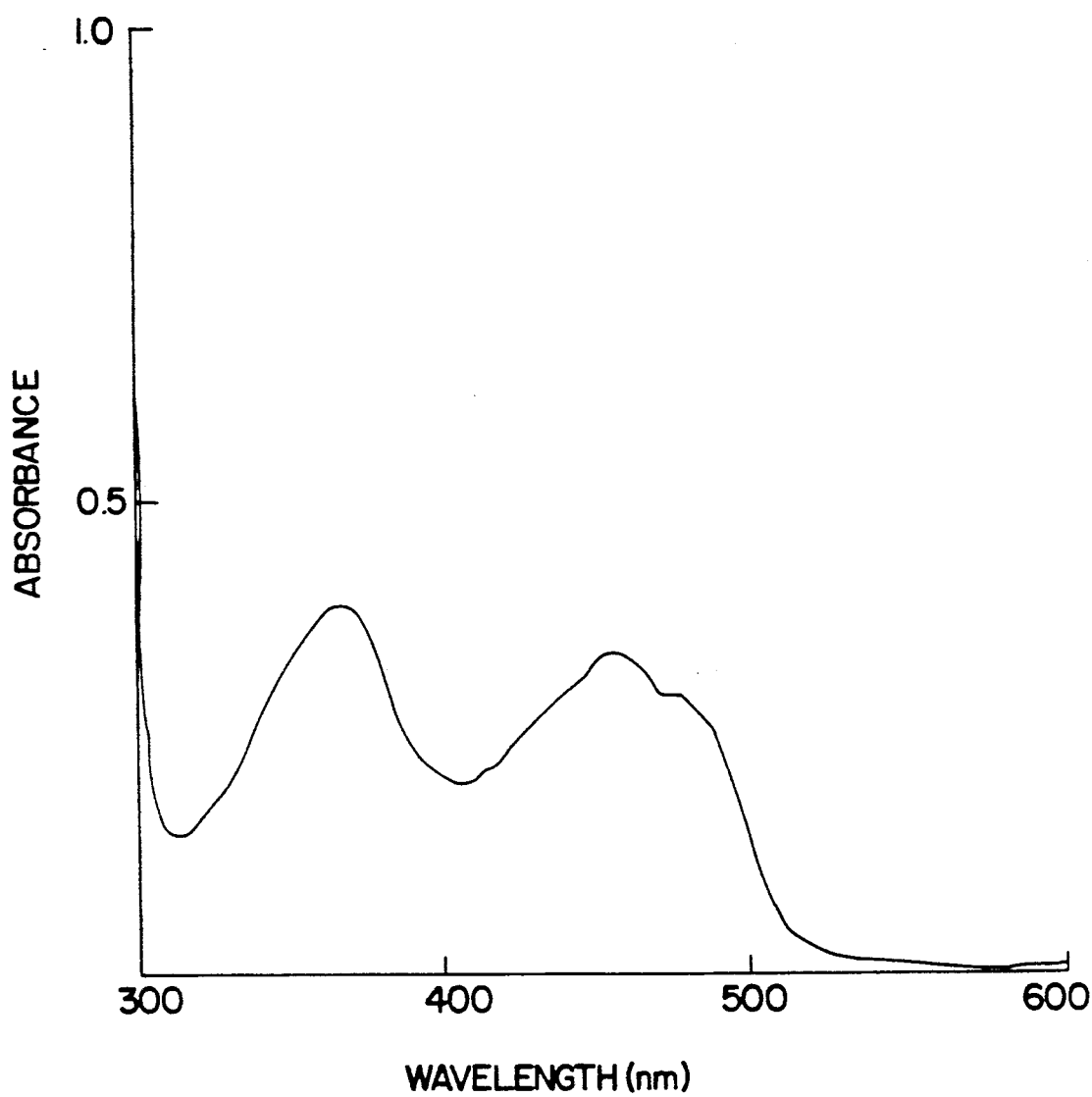
FIG. 8 is an absorption spectrum of the same sample as in FIG. 7 at 10 mg/ml.

The results are shown in FIGS. 7 and 8. The enzyme of the present invention is considered to be a flavine enzyme because it has maximum absorptions at around 275 nm, 370 nm and 453 nm and shows the shoulder at around 480 nm.

The following Examples further illustrate the present invention in detail but are not to be construed to limit the scope thereof. In the Examples, all the "%" in the compositions of culture media are "% (w/v)" unless otherwise stated.

EXAMPLE 1

A culture medium (500 m:) containing yeast extract (0.4%, Daigo Nutritive Chemical Industries, Inc., Japan) malt extract (1.0%, Difco Laboratories, Inc., U.S.A.), dextrin (1.0%), corn steep liuor (1.0%) and choline chloride (1.0%) was adjust to pH 6.5 by adding thereto dropwise 30% aqueous solution of sodium hydroxide. To the medium was added calcium carbonate (2.5 g) and the mixture was placed in a 2-liter Sakaguchi flask, followed by autoclaving at 120° C. for 20 minutes. The medium was inoculated with a slant culture of Streptomyces thermolutenus subsp. fuscus C-19 (IFO 14770, FERM BP-2007), and incubated at 28° C. for 48 hours on a reciprocal shaking device (80 spm).

On the other hand, 80 : of tap water was placed in a 200-liter fermenter. To the fermenter were added dextrin (1.2 kg), Proflo (1.2 kg) (trade name, Trader Oil, Inc., U.S.A.), corn steep liquor (2.4 kg), dipotassium hydrogen phosphate (120 g), magnesium sulfate (24 g), Actocol (240 g) (antifoaming agent, Takeda Chemical and Industries, Ltd., Japan). The mixture was thoroughly stirred to dissolve the above materials and 20% aqueous solution of sodium hydroxide was added dropwise to adjust pH to 6.5. The mixture was then subjected to steam sterilization with stirring under conditions of 100 rpm at 120° C. for 20 minutes, to which was added sterilized water to adjust the volume of the medium to 120 l, followed by cooling to 37° C. This medium was inoculated with the above-prepared culture broth in Sakaguchi flask (500 ml), followed by incubation at 37° C. for 30 hours under conditions of aeration of 2/3 VVM (volume of air/min./unit volume) and inner pressure of 1.0 kg/cm gauge and stirring at 190 rpm.

The culture broth thus obtained (ca. 105 l) was subjected to centrifugation (13000×g) with a Sharples supercentrifuge (AS-16 V type, Sharples Corporation, U.S.A.) to obtain 4.28 kg of wet cells, to which was added 30 l of 0.05M Tris-HCl buffer solution (pH 7.5). The mixture was thoroughly stirred to suspend the cells. The cells were crushed with a homogenizer (LAB 16.51 type, RANNIE A.S., Denmark) under 750 bar for 12 minutes at the maximum temperature of 38.5° C. The resulting crushed cell suspension was again subjected to centrifuge with a continuous centrifuge at 12000×g to remove the solid portion to obtain the supernatant. The solid portion was suspended in 15 l of the above buffer solution and the suspension was thoroughly stirred, which was subjected to centrifugation to collect the supernatant. This supernatant was combined with the above-obtained supernatant to obtain 34 l of a cell extract, to which was added 135 l of ethanol. The mixture was thoroughly stirred and allowed to stand at 5° C. for 24 hours to obtain protein precipitate. The precipitate was separated with the above centrifuge at 13000×g and dried with a freeze-drier (FD-1 type, Tokyo Rika Kikai, Ltd., Japan) at 50 Pa for 24 hours to obtain 400 g of a dry authentic sample. The dry sample was dissolved in 4 l of the above buffer solution. By using a cooling centrifuge (CR 26H type, Hitachi Seisakusho, Japan), the solution was centrifuged at 5000×g at 5° C. for 20 minutes to remove insolubles to obtain 3960 ml of the supernatant. 2508 g of ammonium sulfate was slowly dissolved in the supernatant to salt out the enzyme protein. It was allowed to stand at 5° C. for 14 hours, followed by centrifugation again with a cooling centrifuge at 5000×g at 5° C. for 30 minutes to obtain 267 g of the salted out product. The product was dissolved in 500 ml of the above buffer solution, passed through a column of Sephadex G-25 (inner diameter: 33 mm × 300 cm, Pharmacia Labs., Inc., U.S.A.) and eluted with the above buffer solution to carry out gel-filtration for desalting. 900 ml of the resulting active fraction was adsorbed on a column of DEAE cellulofine A-500 (inner diameter: 30 mm×50 cm, Seikagaku Kogyo, Ltd., Japan). The column was washed with 3 l of the above buffer solution and eluted with 0.1 M NaCl and 0.05 M Tris-HCl buffer solution (pH 7.5). The active fractions (500 m:) were collected and 120 g of ammonium sulfate was dissolved therein. To the solution was added the above buffer solution to adjust the volume to 600 ml and the solution was adsorbed to a hydrophobic chromato-column (Butyl toyopearl 650C, inner diameter: 30 mm×50 cm, Toso. Ltd., Japan). The column was subjected to ion concentration gradient chromatography with 0.05 M Tris-HCl buffer solution containing ammonium sulfate ranging from 20% to 0%. 300 ml of the active fraction was collected and 90 g of ammonium sulfate was dissolved therein to salt out. The salted-out product was separated by a cooling centrifuge at 5000×g at 5° C. for 20 minutes, which was subjected to desalting by using a column of Sephadex G-25. The active fraction thus obtained was adsorbed onto a column of DEAE cellulofine A-500 (inner diameter: 30 mm × 50 cm, Seikagaku Kogyo, Ltd., Japan) and eluted with 0.1 M NaCl and 0.05 M Tris-HCl buffer solution (pH 7.5). The active fraction (360 m:) was subjected to dialysis against 10 l of distilled water at 5° C. The dialyzed solution was freeze-dried with a freeze-drier (FD-1 Type, Tokyo Rika Kikai, Ltd., Japan) at 30 Pa to obtain 250 mg of a dry authentic sample of choline oxidase.

TABLE 4

| Purification step | Total Activity (U) | Total Protein (mg) | Specific Activity (U/mg) |
|---|---|---|---|
| Cell extract | 11,500 | 95,833 | 0.12 |
| Ethanol precipitation | 10,560 | 23,457 | 0.45 |
| Ammonium sulfate salting out | 9,951 | 9,046 | 1.10 |
| Sephadex G-25 (1) | 9,230 | 8,168 | 1.13 |
| DEAE cellulofine (1) | 6,790 | 1,167 | 5.82 |
| Hydrophobic chromatography | 3,433 | 426 | 8.05 |
| Sephadex G-25 (2) | 3,077 | 365 | 8.43 |
| DEAE cellulofine (2) | 2,375 | 268 | 8.86 |
| Dry authentic sample | 2,215 | 250 | 8.86 |

The total activity, the amount of total protein and the specific activity of choline oxidase in each purification step are shown in the above Table 4.

The method for determining the activity was that described in the above and the determination of protein was carried out according to the method for determination of BCA protein (Analytical Biochemistry, Vol. 150, pp 76–85, 1985). The purified authentic sample of the enzyme thus obtained showed the single band of homogeneous protein by the method of electrophoresis described above.

EXAMPLE 2

A culture medium (500 ml) containing yeast extract (0.4%, Daigo Nutritive Chemical Industries. Ltd., Japan). malt extract (1.0%, Difco Laboratories, Inc. U.S.A.), dextrin (1.0%) and corn steep liuor (1.0%) was adjusted to pH 6.5 by adding thereto dropwise 20% aqeous solution of sodium hydroxide. To the medium was added 2.5 g of calcium carbonate and the mixture was placed in a 2-liter Sakaguchi flask followed by autoclaving at 120° C. for 20 minutes. The medium was inoculated with a slant culture of Streptomyces thermoluteus subsp. fuscus C-19 (IFO 14770, FERM BP-2007) and incubated at 28° C. for 48 hours on a reciprocal shaking device (80 spm).

On the other hand, 80 l of tap water was placed in a 200-liter fermenter. To the fermenter were added dextrin (1.2 kg), Proflo (1.2 kg, trade name, Trader Oil, Inc., U.S.A.), corn steep liquor (2.4 kg), dipotassium hydrogen phosphate (120 g), magnesium sulfate (24 g) and Actocol (240 g) and the mixture was thoroughly stirred to dissolve the above materials, to which was added dropwise 20% aqueous solution of sodium hydroxide to adjust its pH to 6.5. The mixture was then subjected to steam sterilization with stirring at 100 rpm at 120° C. for 20 minutes and sterilized water was added thereto to adjust the volume of the medium to 120 l, followed by cooling to 37° C. This medium was inoculated with the above-prepared culture broth in Sakaguchi flask (500 ml), followed by incubation at 37° C. for 30 hours under conditions of aeration of ⅔ VVM (volume of air/min./unit volume), inner pressure of 1.0 kg/cm gauge and stirring at 190 rpm.

The culture broth (ca. 108 l) thus obtained was subjected to centrifugation (13000×g) with a Sharples supercentrifuge (AS-16 V type, Sharples Corporation, U.S.A.) to obtain 3.98 kg of wet cells, to which was added 30 l of 0.05 M Tris-HCl buffer solution (pH 7.5). The mixture was thoroughly stirred to suspend the cells. The cells were crushed with a homogenizer (LAB 16.51 type, RANNIE A.S., Denmark) under 750 bar for 12 minutes at the maximum temperature of 38.5° C. The resulting crushed cell suspension was again subjected to centrifugation with a continuous centrifuge at 13000×g to remove the solid portion to leave the supernatant. The solid portion was suspended in 15 l of the above buffer solution and the suspension was thoroughly stirred, which was subjected to centrifugation to collect the supernatant. This supernatant was combined with the above supernatant to obtain 33 l of a cell extract, to which was added 134 l of ethanol. The mixture was thoroughly stirred and allowed to stand at 5° C. for 24 hours to obtain protein precipitate. The precipitate was separated with the above centrifuge at 13000×g and dried with a freeze-drier (FD-1 type, Tokyo Rika Kikai, Ltd., Japan) at 50 Pa for 24 hours to obtain 351 g of a dry authentic sample. The dry sample was dissolved in 4 l of the above buffer solution. By using a cooling centrifuge (CR 26H type, Hitachi Seisakusho, Japan), this solution was subjected to centrifugation at 5000×g at 5° C. for 20 minutes to remove insolubles to obtain 3940 ml of the supernatant. 2500 g of ammonium sulfate was slowly dissolved in this supernatant to salt out the enzyme protein. It was allowed to stand at 5° C. for 14 hours, followed by subjecting again to centrifugation with a cooling centrifuge at 5000×g at 5° C. for 30 minutes to obtain 299 g of the salted-out product. The product was dissolved in 500 m: of the above buffer solution, passed through a column of Sephadex G-25 (inner diameter: 33 mm×300 cm, Pharmacia Labs., Inc., U.S.A.) and eluted with the above buffer solution to effect desalting. 750 ml of the active fraction thus obtained was adsorbed on a column of DEAE cellulofine A-500 (inner diameter: 30 mm×50 cm, Seikagaku Kogyo, Ltd., Japan). The column was washed with 3 l of the above buffer solution and eluted with 0.1 M NaCl and 0.05 M Tris-HCl buffer solution (pH 7.5). Active fractions (480 ml) were collected and 120 g of ammonium sulfate was dissolved therein. To the solution was added the above buffer solution to adjust the volume to 600 ml and adsorbed to a hydrophobic chromatocolumn (Butyl toyopearl 650C, inner diameter: 30 mm×50 cm, Toso Ltd., Japan). The column was subjected to ion concentration gradient chromatography by using 0.05 M Tris-HCl buffer solution containing ammonium sulfate ranging from 20% to 0%. 300 ml of the active fraction was collected in which was dissolved 90 g of ammonium sulfate to cause salting out. The salted-out product was separated by centrifugation with a cooling centrifuge at 5000×g at 5° C. for 20 minutes, which was subjected to desalting using a column of Sephadex G-25. The active fraction thus obtained was adsorbed to a column of DEAE cellulofine A-500 (inner diameter: 30 mm×50 cm, Seikagaku Kogyo, Ltd., Japan) and eluted with 0.1 M NaCl and 0.05 M Tris-HCl buffer solution (pH 7.5). The active fraction (157 ml) was subjected to dialysis against 10 l of distilled water at 5° C. The dialyzed solution was freeze-dried with a freeze-drier (FD-1 Type, Tokyo Rika Kikai, Ltd., Japan) at 30 Pa to obtain 79 mg of a dry authentic sample of choline oxidase. The specific activity of the dry authentic sample was 8.55 U/mg. According to the above electrophoresis, the sample showed the band of a single homogeneous protein.

EXAMPLE 3

A culture medium (500 ml) containing yeast extract (0.4%, Daigo Nutritive Chemical Industries. Ltd., Japan), maltose extract (1.0%, Difco Laboratories, Inc. U.S.A.), dextrin (1.0%), corn steep liquor (1.0%) and choline chloride (1.0%) was adjusted to pH 6.5 by adding thereto dropwise 20% aqueous solution of sodium hydroxide. To the medium was added 2.5 g of calcium carbaonate and the mixture was placed in a 2-liter Sakaguchi flask, followed by autoclaving at 120° C. for 20 minutes. The medium was inoculated with a slant culture of Streptomyces thermoluteus subsp. fuscus IFO 14270 and incubated at 28° C. for 48 hours on a reciprocal shaking device (80 spm).

On the other hand, 80 l of tap water was placed in a 200-liter fermenter. To the fermenter were added dextrin (1.2 kg), Proflo (1.2 kg, trade name, Trader Oil, Inc., U.S.A.), corn steep liquor (2.4 kg), choline chloride (2.4 kg), dipotassium hydrogen phosphate (120 g), magnesium sulfate (24 g) and Actocol (240 g). The mixture was thoroughly stirred to dissolved the materials and to the solution was added dropwise 20% aqueous solution of sodium hydroxide to adjust its pH to 6.5. The mixture was then subjected to steam sterilization with stirring at 100 rpm at 120° C. for 20 minutes, to which was added sterilized water to adjust the volume of the medium to 120 l, followed by cooling to 37° C. This medium was inoculated with the above-prepared culture broth in Sakaguchi flask (500 ml), followed by incubation at 37° C. for 120 hours under conditions of aeration of ⅔ VVM (volume of air/min./unit volume), inner pressure of 1.0 kg/cm gauge and stirring at 190 rpm.

The culture broth (ca. 105 l) thus obtained was subjected to centrifugation (13000×g) with a Sharples supercentrifuge (AS-16 V type, Sharples Corporation, U.S.A.) to obtain 4.03 kg of wet cells, to which was added 30 l of a 0.05 M Tris-HCl buffer solution (pH 7.5). The mixture was thoroughly stirred to suspend the cells. The cells were crushed with a homogenizer (LAB 16.51 type, RANNIE A.S., Denmark) at 750 bar for 12 minutes at the maximum temperature of 38.5° C. The resulting crushed cell suspension was again subjected to centrifugation with a continuous centrifuge under the conditions of 13000×g to remove the solid portion to leave the supernatant. The solid portion was suspended in 15 l of the above buffer solution and the suspension was thoroughly stirred, which was subjected to centrifugation to collect the supernatant. This supernatant was combined with the above supernatant to obtain 34 l of a cell extract solution, to which added 135 l of ethanol. The mixture was thoroughly stirred and allowed to stand at 5° C. for 24 hours to obtain protein precipitate. The precipitate was separated with the above centrifuge at 13000×g and dried with a freeze-drier (FD-1 type, Tokyo Rika Kikai, Ltd., Japan) at 50 Pa for 24 hours to obtain 380 g of a dry authentic sample. The dry sample was dissolved in 4 l of the above buffer solution. By using a cooling centrifugal machine (CR 26H type, Hitachi Seisakusho, Japan), this solution was subjected to centrifugation at 5000×g at 5° C. for 20 minutes to remove insolubles to obtain 3880 ml of the supernatant. 2500 g of ammonium sulfate was slowly dissolved therein to salt out the enzyme protein, which was allowed to stand at 5° C. for 14 hours, followed by subjecting again to centrifugation with a cooling centrifuge at 5000×g at 5° C. for 30 minutes to obtain 252 g of the salted-out product. The product was dissolved in 500 ml of the above buffer solution, passed through a column of Sephadex G-25 (inner diameter: 33 mm×300 cm, Pharmacia Labs., Inc., U.S.A.) and eluted with the above buffer solution to effect desalting. 900 ml of the active fraction thus obtained was adsorbed on a column of DEAE cellulofine A-500 (inner diameter: 30 mm×50 cm, Seikagaku Kogyo, Ltd., Japan). The column was washed with 3 l of the above buffer solution and eluted with 0.1 M NaCl and 0.05 M Tris-HCl buffer solution (pH 7.5). Active fractions (500 ml) were collected and 120 g of ammonium sulfate was dissolved therein. To the solution was added the above buffer solution to adjust the whole volume to 600 ml and adsorbed onto a hydrophobic chromatography column (Butyl toyopearl 650C, inner diameter: 30 mm×50 cm, Toso, Ltd., Japan). The column was subjected to ion concentration gradient chromatography by using 0.05 M Tris-HCl buffer solution containing ammonium sulfate ranging from 20% to 0%. 300 ml of the active fraction was collected and 90 g of ammonium sulfate was dissolved therein to cause salting out. The salted-out product was separated by centrifugation with a cooling centrifuge at 5000×g at 5° C. for 20 minutes, which was subjected to desalting using a column of Sephadex G-25. The active fraction thus obtained was adsorbed to a column of DEAE cellulofine A-500 (inner diameter: 30 mm×50 cm, Seikagaku Kogyo, Ltd., Japan) and eluted with 0.1 M NaCl and 0.05 M Tris-HCl buffer solution (pH 7.5). The active fraction (260 ml) was subjected to dialysis against 10 l of distilled water at 5° C. The dialyzed solution was freeze-dried with a freeze-drier (FD-1 Type, Tokyo Rika Kikai, Ltd., Japan) at 30 Pa to obtain 180 mg of a dry authentic sample of choline oxidase. The specific activity of the dry authentic sample was 8.81 U/mg. According to the above electrophoresis, the sample showed the band of a single homogeneous protein.

EXAMPLE 4

A culture medium (500 ml) containing yeast extract (0.4%, Daigo Nutritive Chemical Industries. Ltd., Japan), malt extract (1.0%, Difco Laboratories, Inc. U.S.A.), dextrin (1.0%) and corn steep liquor (1.0%) was adjusted to pH 6.5 by adding thereto dropwise 20% aqueous solution of sodium hydroxide. To the medium was added 2.5 g of calcium carbonate and the mixture was placed in a 2-liter Sakaguchi flask, followed by autoclaving at 120° C. for 20 minutes. The medium was inoculated with a slant culture of *Streptomyces thermoluteus subsp. fuscus* and incubated at 28° C. for 48 hours on a reciprocal shaking device (80 spm).

On the other hand, 80 l of tap water was placed in a 200-liter fermenter. To the fermenter were added dextrin (1.2 kg), Proflo (1.2 kg, trade name, Trader Oil, Inc., U.S.A.), corn steep liquor (2.4 kg), casein (1.2 kg), dipotassium hydrogen phosphate (120 g), magnesium sulfate (24 g) and Actocol (240 g). The mixture was thoroughly stirred to dissolve the materials, to which was added dropwise a 20% aqueous solution of sodium hydroxide to adjust its pH to 6.5. The mixture was then subjected to steam sterilization with stirring at 100 rpm at 120° C. for 20 minutes, to which was added sterilized water to adjust the volume of the medium to 120 l, followed by cooling to 37° C. This medium was inoculated with the above culture broth in Sakaguchi flask (500 ml), followed by incubation at 0 37° C. for 42 hours under conditions of aeration ⅜ VVM (volume of air/min./unit volume), inner pressure of 1.0 kg/cm gauge and stirring at 190 rpm.

The culture broth (ca. 107 l) thus obtained was subjected to centrifugation (13000×g) with a Sharples supercentrifuge (AS-16 V type, Sharples Corporation, U.S.A.) to obtain 3.90 kg of wet cells, to which was added 30 l of a 0.05M Tris-HCl buffer solution (pH 7.5). The mixture was thoroughly stirred to suspend the cells. Then, the suspended cells were crushed with a homogenizer (LAB 16.51 type, RANNIE A.S., Denmark) under 750 bar for 12 minutes at the maximum temperature of 38.5° C. The resulting crushed cell suspension was again subjected to centrifugation with a continuous centrifuge under the conditions of 13000×g to remove the solid portion to leave the supernatant. The solid portion was suspended in 15 l of the above buffer solution and the suspension was thoroughly stirred, which was subjected to centrifugation to collect the supernatant. This supernatant was combined with the above supernatant to obtain 33 l of a cell extract, to which was added 134 l of ethanol. The mixture was thoroughly stirred and allowed to stand at 5° C. for 24 hours to obtain protein precipitate. The precipitate was separated with the above centrifuge the conditions of 13000×g and dried with a freeze-drier (FD-1 type, Tokyo Rika Kikai, Ltd., Japan) under the conditions of 50 Pa for 24 hours to obtain 345 g of a dry authentic sample. The dry sample was dissolved in 4 l of the above buffer solution. By using a cooling centrifuge (CR 26H type, Hitachi Seisakusho, Japan), this solution was subjected to centrifugation under the conditions of 5000×g at 5° C. for 20 minutes to remove insolubles to obtain 3830 ml of the supernatant. In this supernatant was slowly dissolved 2500 g of ammonium sulfate to salt out the enzyme protein. It was allowed to stand at 5° C. for 14 hours, followed by subjecting again to centrifugation with a cooling centrifuge under the conditions of 5000×g at 5° C. for 30 minutes to obtain 215 g of the salted-out product. The product was dissolved in 500 ml of the above buffer solution, passed through a column of Sephadex G-25 (inner diameter: 33 mm×300 cm, Pharmacia Labs., Inc., U.S.A.) and eluted with the above buffer solution to effect desalting. 750 ml of the active fraction thus obtained was adsorbed on a column of DEAE cellulofine A-500 (inner diameter: 30 mm×50 cm, Seikagaku Kogyo, Ltd., Japan). The column was washed with 3 l of the above buffer solution and eluted with 0.1 M NaCl and a 0.05 M Tris-HCl buffer solution (pH 7.5). Active fractions (470 ml) were collected and 120 g of ammonium sulfate was dissolved therein. To the solution was added the above buffer solution to make the whole volume 600 ml, which was adsorbed on a hydrohobic chromato-column (Butyl toyopearl 650C, inner diameter: 30 mm×50 cm, Toso, Ltd., Japan). The column was subjected to ion-concentration gradient chromatography by using 0.05 M Tris-HCl buffer solutions containing ammonium sulfate ranging from 20% to 0%. 300 ml of the active fraction was collected in which was dissolved 90 g of ammonium sulfate to cause salting out. The salted-out product was separated by centrifugation under the conditions of 5000×g at 5° C. for 20 minutes and subjected to desalting using a column of Sephadex G-25. The active fraction thus obtained was adsorbed to a column of DEAE cellulofine A-500 (inner diameter: 30 mm×50 cm, Seikagaku Kogyo, Ltd., Japan) and eluted with 0.1 M NaCl and a 0.05 M Tris-HCl buffer solution (pH 7.5). The active fraction (141 ml) was subjected to dialysis against 10 l of distilled water at 5° C. The dialyzed solution was freeze-dried with a freeze-drier (FD-1 Type, Tokyo Rika Kikai, Ltd., Japan) under the conditions of 30 Pa to obtain 57 mg of a dry authentic sample of choline oxidase. The specific activity of the dry authentic sample was 8.51 U/mg. According to the above electrophoresis, the sample showed the band of a single uniform protein.

EXAMPLE 5

A culture medium (500 ml) containing yeast extract (0.4%, Daigo Nutritive Chemical Industries, Ltd., Japan), maltose extract (10%, Difco Laboratories, Inc., U.S.A.), dextrin (1.0%), corn steep liquor (1.0%) and choline chloride (1.0%) was adjust to pH 6.5 by adding thereto dropwise a 20% aqueous solution of sodium hydroxide. To the medium was added 2.5 g of calcium carbonate and the mixture was placed into a 2-liter Sakaguchi flask, followed by autoclaving at 120° C. for 20 minutes. The medium was inoculated with a slant culture of *Themoactinomyces monosporus* IFO 14050, which was incubated at 43° C. for 48 hours on a reciprocal shaking device (80 spm).

On the other hand, 80 l of tap water was placed in a 200-liter fermenter. To the fermenter were added dextrin (6.0 kg), Proflo (1.2 kg) (trade name, Trader Oil, Inc., U.S.A.), corn steep liquor (2.4 kg), casein (1.2 kg), choline chloride (2.4 kg), dipotassium hydrogen phosphate (120 g), magnesium sulfate (24 g) and Actocol (240 g). The mixture was thoroughly stirred to dissolve the materials, to which was added dropwise a 20% aqueous solution of sodium hydroxide to adjust its pH to 6.5. The mixture was then subjected to steam sterilization with stirring under conditions of 100 rpm at 120° C. for 20 minutes. Sterilized water was added thereto to make the volume of the medium 120 l followed by cooling to 43° C. This medium was inoculated with the above culture broth in Sakaguchi flask (500 ml), followed by incubation at 43° C. for 90 hours under conditions of aeration of $\frac{2}{3}$ VVM (volume of air/min./unit volume), inner pressure of 1.0 kg/cm gauge and stirring at 190 rpm.

The culture broth thus obtained (ca. 105 l) was subjected to centrifugation (13000×g) with a Sharples supercentrifuge (AS-16 V type, Sharples Corporation, U.S.A.) to obtain 3.82 kg of wet cells, to which was added 30 l of a 0.05 M Tris-HCl buffer solution (pH 7.5). The mixture was thoroughly stirred to suspend the cells. The suspended cells were crushed with a homogenizer (LAB 16.51 type, RANNIE A.S., Denmark) under 750 bar for 12 minutes at the maximum temperature of 38.5° C. The resulting crushed cell suspension was again subjected to centrifugation with a continuous centrifuge under the conditions of 13000×g to remove the solid portion to leave the supernatant. The solid portion was suspended in 15 l of the above buffer solution and the suspension was thoroughly stirred, which was subjected to centrifugation to collect the supernatant. This supernatant was combined with the above supernatant to obtain 29 l of a cell extract, to which was added 135 : of ethanol. The mixture was thoroughly stirred and allowed to stand at 5° C. for 24 hours to obtain protein precipitate. The precipitate was separated with the above centrifuge under the conditions of 13000×g and dried with a freeze-drier (FD-1 type, Tokyo Rika Kikai, Ltd., Japan) under the conditions of 50 Pa for 24 hours to obtain 310 g of an authentic sample of crude enzyme. This sample was subjected to determination of its activity by means of the above method for determination of choline oxidase. As the result, the specific activity was 0.05 U/mg. The thermostability of this enzyme was shown in FIGS. 4 and 5.

EXAMPLE 6

A culture medium (500 ml) containing yeast extract (0.4%, Daigo Nutritive Chemical Industries, Ltd.), maltose extract (10%, Difco Laboratories, Inc., U.S.A.), dextrin (1.0%), corn steep liquor (1.0%) and choline chloride (1.0%) was adjust to pH 6.5 by adding thereto dropwise a 20% aqueous solution of sodium hydroxide. To the medium was added 2.5 g of calcium carbonate and the medium was placed in 2-liter Sakaguchi flask, followed by subjecting autoclaving at 120° C. for 20 minutes. The medium was inoculated with a slant culture of *Streptomyces thermophilus* IFO 13370, which was incubated at 28° C. for 48 hours on a reciprocal shaking device (80 spm).

On the other hand, 80 l of tap water was place into a 200-liter fermenter. To the fermenter were added dextrin (6.0 kg), Proflo (1.2 kg) (trade name, Trader Oil, Inc., U.S.A.), corn steep liquor (2.4 kg), casein (1.2 kg), choline chloride (2.4 kg), dipotassium hydrogen phosphate (120 g), magnesium sulfate (24 g) and Actocol (240 g). The mixture was thoroughly stirred to dissolved the materials, to which was added dropwise a 20% aqueous solution of sodium hydroxide to adjust its pH to 6.5. The mixture was then subjected to steam sterilization with stirring under conditions of 100 rpm at 120° C. for 20 minutes, to which was added sterilized water to make the volume of the medium 120 l, followed by cooling to 37° C. This medium was inoculated with the above culture broth in Sakaguchi flask (500 ml), followed by incubation at 37° C. for 90 hours under conditions of aeration of $\frac{2}{3}$ VVM (volume of air/min./unit volume), inner pressure of 1.0 kg/cm gauge and stirring at 190 rpm.

The culture broth thus obtained (ca. 105 l) was subjected to centrifuge (13000×g) with a Sharples supercentrifuge (AS-16 V type, Sharples Corporation, U.S.A.) to obtain 3.42 kg of wet cells, to which was added 30 l of a 0.05 M Tris-HCl buffer solution (pH 7.5). The mixture was thoroughly stirred to suspend the cells. The suspended cells were crushed with a homogenizer (LAB 16.51 type, RANNIE A.S., Denmark) under 750 bar for 12 minutes at the maximum temperature of 38.5° C. The resulting cell suspension was again subjected to centrifugation with a continuous centrifuge under the conditions of 13000×g to remove the solid portion to leave the supernatant. The solid portion was suspended in 15 l of the above buffer solution and the suspension was thoroughly stirred, which was subjected to centrifugation to collect the supernatant. This supernatant was combined with the above supernatant to obtain 30 l of a cell extract, to which was added 135 l of ethanol. The mixture was thoroughly stirred and allowed to stand at 5° C. for 24 hours to obtain protein precipitate. The precipitate was separated with the above centrifuge under the condition of 13000×g and dried with a freeze-drier (FD-1 type, Tokyo Rika Kikai Ltd., Japan) under the conditions of 50 Pa for 24 hours to obtain 310 g of an authentic sample of crude enzyme. This sample was subjected to determination of its activity by means of the above method for determination of choline oxidase. As the result, the specific activity was 0.16 U/mg. The thermostability of this enzyme was shown in FIGS. 4 and 5.

EXAMPLE 7

A culture medium (500 ml) containing yeast extract (0.4%, Daigo Nutritive Chemical Industries, Ltd., Japan), maltose extract (10%, Difco Laboratories, Inc., U.S.A.), dextrin (1.0%), corn steep liquor (1.0%) and choline chloride (1.0%) was adjust to pH 6.5 by adding thereto dropwise a 20% aqueous solution of sodium hydroxide. To the medium was added 2.5 g of calcium carbonate and the mixture was placed into a 2-liter Sakaguchi flask, followed by autoclaiving at 120° C. for 20 minutes. The medium was inoculated with a slant culture of *Saccharopolyspora hirsuta* ATCC 27876, which was incubated at 37° C. for 30 hours under a reciprocal shaking device (80 spm).

On the other hand, 80 l of tap water was placed into a 200-liter fermenter. To the fermenter were added dextrin (6.0 kg), Proflo (1.2 kg) (trade name, Trader Oil, Inc., U.S.A.), corn steep liquor (2.4 kg), casein (1.2 kg), choline chloride (2.4 kg), potassium phosphate (120 g), magnesium sulfate (24 g) and Actocol (240 g). The mixture was thoroughly stirred to dissolve the materials, to which was added dropwise a 20% aqueous solution of sodium hydroxide to adjust its pH to 6.5. The mixture was then subjected to steam sterilization with stirring under conditions of 100 rpm at 120° C. for 20 minutes. Sterilized water was added thereto to make the volume of the medium 120 l, followed by cooling to 37° C. This medium was inoculated with the above culture broth in Sakaguchi flask (500 ml), followed by incubation at 37° C. for 30 hours under conditions of aeration of ⅔ VVM (volume of air/min./unit volume), inner pressure of 1.0 kg/cm gauge and stirring at 190 rpm.

Figure 9:
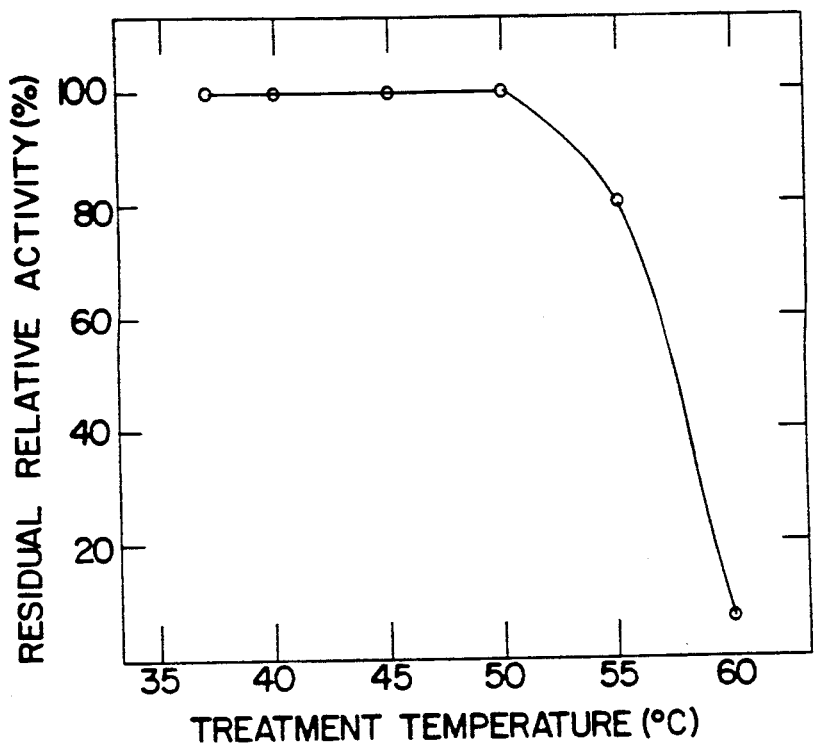
FIG. 9 is a graph illustrating residual activities of choline oxidases obtained in Examples 7, 8 and 9, after heating for 15 minutes at various temperatures.

The culture broth thus obtained (ca. 105 l) was subjected to centrifugation (13000×g) with a Sharples supercentrifuge (AS-16 V type, Sharples Corporation, U.S.A.) to obtain 4.02 kg of wet cells, which were suspended in 30 l of a 0.05 M Tris-HCl buffer solution (pH 7.5). The suspension was placed in a 50 l reactor equipped with a stirrer and a jacket, to which was added 100 g of crystalline lysozyme chloride (manufactured by Nagase Seikagaku Kogyo, Ltd., Japan). The mixture was stirred to dissolve the lysozyme chloride. The suspension was stirred at 37° C. for 2 hours to dissolve cell walls. The resulting solution was again subjected to centrifugation with a continuous centrifuge under the conditions of 13000×g to remove the solid portion to leave a supernatant. The solid portion was suspended in 15 l of the above buffer solution and the suspension was thoroughly stirred, which was subjected to centrifugation to collect the supernatant. This supernatant was combined with the above supernatant to obtain 31 l of a cell extract, to which was added 135 l of ethanol. The mixture was thoroughly stirred and allowed to stand at 5° C. for 24 hours to obtain protein precipitate. The precipitate was separated with the above centrifuge under the conditions of 13000×g and dried with a freeze-drier (FD-1 type, Tokyo Rika Kikai, Ltd., Japan) under the conditions of 50 Pa for 24 hours to obtain 387 g of an authentic sample of crude enzyme. This sample was subjected to determination of its activity by means of the above method for determination of choline oxidase. As the result, the specific activity was 0.43 U/mg. The thermostability of this enzyme was shown in FIGS. 5 and 9.

EXAMPLE 8

A culture medium (500 ml) containing yeast extract (0.4%, Daigo Nutritive Chemical Industries, Ltd., Japan), maltose extract (10%, Difco Laboratories, Inc., U.S.A.), dextrin (1.0%), corn steep liquor (1.0%) and choline chloride (1.0%) was adjust to pH 6.5 by adding thereto dropwise a 20% aqueous solution of sodium hydroxide. To the medium was added 2.5 g of calcium carbonate and the mixture was placed into a 2-liter Sakaguchi flask, followed by autoclaving at 120° C. for 20 minutes. The medium was inoculated with a slant culture of *Saccharopolyspora hirsuta* ATCC 20501, which was incubated at 37° C. for 30 hours on a reciprocal shaking device (80 spm).

On the other hand, 80 l of tap water was placed into a 200-liter fermenter. To the fermenter were added dextrin (6.0 kg), Proflo (1.2 kg) (trade name, Trader Oil, Inc., U.S.A.), corn steep liquor (2.4 kg), casein (1.2 kg), choline chloride (2.4 kg), dipotassium hydrogen phosphate (120 g), magnesium sulfate (24 g) and Actocol (240 g). The mixture was thoroughly stirred to dissolve the materials, to which was added dropwise a 20% aqueous solution of sodium hydroxide to adjust its pH to 6.5. The mixture was then subjected to steam sterilization with stirring under conditions of 100 rpm at 120° C. for 20 minutes, to which was added sterilized water to make the volume of the medium 120 l, followed by cooling to 37° C. This medium was inoculated with the above culture broth in Sakaguchi flask (500 ml), followed by incubation at 37° C. for 90 hours under conditions of aeration of ⅔ VVM (volume of air/min./unit volume), inner pressure of 1.0 kg/cm gauge and stirring at 190 rpm.

The culture broth thus obtained (ca. 105 l) was subjected to centrifugation (13000×g) with a Sharples supercentrifuge (AS-16 V type, Sharples Corporation, U.S.A.) to obtain 3.91 kg of wet cells, which was suspended in 30 l of a 0.05 M Tris-HCl buffer solution (pH 7.5). The suspension was placed in a 50 l reactor equipped with a stirrer and a jacket, to which was added 100 g of crystalline lysozyme chloride (manufactured by Nagase Seikagaku Kogyo, Ltd., Japan). The mixture was stirred to dissolve the lysozyme chloride. The suspension was stirred at 37° C. for 2 hours to dissolve cell walls. The resulting solution was again subjected to centrifugation by means of a continuous centrifuge under the conditions of 13000×g to remove the solid portion to leave a supernatant. The solid portion was suspended in 15 l of the above buffer solution, and the suspension was thoroughly stirred, which was subjected to centrifugation to collect the supernatant. This supernatant was combined with the above supernatant to obtain 30 l of a cell extract, to which was added 135 l of ethanol. The mixture was thoroughly stirred and allowed to stand for 24 hours at 5° C. to obtain protein precipitate. The precipitate was separated with the above centrifuge under the conditions of 13000×g and dried with a freeze-drier (FD-1 type, Tokyo Rika Kikai, Ltd., Japan) under the conditions of 50 Pa for 24 hours to obtain 330 g of an authentic sample of crude enzyme. This sample was subjected to determination of its activity by means of the above method for determination of choline oxidase. As the result, the specific activity was 0.12 U/mg. The thermostability of this enzyme was shown in FIGS. 5 and 9.

EXAMPLE 9

A culture medium (500 ml) containing yeast extract (0.4%, Daigo Nutritive Chemical Industries, Ltd., Japan), maltose extract (10%, Difco Laboratories, Inc., U.S.A.), dextrin (1.0%), corn steep liquor (1.0%) and choline chloride (1.0%) was adjust to pH 6.5 by adding thereto dropwise a 20% aqueous solution of sodium hydroxide. To the medium was added 2.5 g of calcium carbonate and the mixture was placed in a 2-liter Sakaguchi flask, followed by autoclaving at 120° C. for 20 minutes. The medium was inoculated with a slant culture of *Saccharopolyspora hirsuta* IFO 13919, which was incubated at 37° C. for 30 hours under a reciprocal shaking device (80 spm).

On the other hand, 80 l of tap water was placed into a 200-liter fermenter. To the fermenter were added dextrin (6 kg), Proflo (1.2 kg) (trade name, Trader Oil, Inc., U.S.A.), corn steep liquor (2.4 kg), casein (1.2 kg), choline chloride (2.4 kg), dipotassium hydrogen phosphate (120 g), magnesium sulfate (24 g), and Actocol (240 g). The mixture was thoroughly stirred to dissolve the materials, to which was added dropwise a 20% aqueous solution of sodium hydroxide to adjust its pH to 6.5. The mixture was then subjected to steam sterilization with stirring under conditions of 100 rpm at 120° C. for 20 minutes, to which was added sterilized water to make the volume of the medium 120 l followed by cooling to 37° C. This medium was inoculated with the above culture broth in Sakaguchi flask (500 ml), followed by incubation at 37° C. for 90 hours under conditions of aeration $\frac{1}{3}$ VVM (volume of air/min./unit volume), inner pressure of 1.0 kg/cm gauge and stirring at 190 rpm.

The culture broth thus obtained (ca. 105 l) was subjected to centrifugation (13000×g) with a Sharples supercentrifuge (AS-16 V type, Sharples Corporation, U.S.A.) to obtain 3.95 kg of wet cells, which were suspended in 30 of a 0.05 M Tris-HCl buffer solution (pH 7.5). The suspension was placed in a 50 l reactor equipped with a stirrer and a jacket, to which was added 100 g of crystalline lysozyme chloride (manufactured by Nagase Seikagaku Kogyo, Ltd., Japan). The mixture was stirred to dissolve the lysozyme chloride. The suspension was stirred at 37° C. for 2 hours to dissolve cell walls. The resulting solution was again subjected to centrifugation by means of a continuous centrifuge under the conditions of 13000×g to remove the solid portion to leave a supernatant. The solid portion was suspended in 15 r of the above buffer solution, and the suspension was thoroughly stirred, which was subjected to centrifugation to collect the supernatant. This supernatant was combined with the above supernatant to obtain 30 l of a cell extract, to which was added 135 l of ethanol. The mixture was thoroughly stirred and allowed to stand at 5° C. for 24 hours at 5° C. to obtain protein precipitate. The precipitate was separated with the above centrifuge under the conditions of 13000×g and dried with a freeze-drier (FD-1 type, Tokyo Rika Kikai, Ltd., Japan) under the conditions of 50 Pa for 24 hours to obtain 338 g of an authentic sample of crude enzyme. This sample was subjected to determination of its activity by means of the above method for determination of choline oxidase. As the result, the specific activity was 0.35 U/mg. The thermostability of this enzyme was shown in FIGS. 5 and 9.

EXAMPLE 10

The crude enzyme obtained in Example 5 (300 g) was dissolved in the above buffer solution (4 l) and centrifuged with a cooling centrifuge (CR26H Type, Hitachi Seisakusho, Co., Ltd., Japan) at 5000×g at 5° C. for 20 minutes to remove insolubles to obtain a supernatant (3960 ml). Ammonium sulfate (2580 g) was slowly dissolved in this supernatant to salt-out enzyme protein. After standing at 5° C. for 14 hours, the supernatant was again centrifuged at 5000×g at 5° C. for 30 minutes to obtain a salted-out product (200 g). The product was dissolved in the above buffer solution (500 ml), passed through Sephadex G-25 column (inner diameter: 33 mm×300 cm, Pharmacia Labs. Inc., U.S.A.) and eluted with the above buffer solution to conduct gel-filtration for desalting to obtain an active fraction (900 ml). The active fraction was adsorbed on DEAE Cellulofine A-500 column (inner diameter: 30 mm×50 cm, Seikagaku Kogyo, Ltd., Japan), washed with the above buffer solution (3 l) and eluted with 0.1 M NaCl, 0.05 M Tris-HCl buffer (pH 7.5). Active fractions (500 ml) were collected and ammonium sulfate (120 g) was dissolved therein. To the solution was added the above buffer solution to make the whole volume 600 ml, which was adsorbed on a hydrophobic chromatography column (Butyl toyopearl 650C, inner diameter: 30 mm×50 cm, Toso, Ltd., Japan). The column was subjected to ion-concentration gradient chromatography by using 0.05 M Tris-HCl buffer solution containing ammonium sulfate ranging from 20% to 0%. Active fractions (300 ml) were collected and ammonium sulfate (90 g) was dissolved therein to effect salting out. The salted-out product was separated by a cooling centrifuge under conditions of 5000×g at 5° C. for 20 minutes, which was further subjected to desalting by using a column of Sephadex G-25. The active fraction thus obtained was adsorbed on a column of DEAE cellulofine A-500 (inner diameter: 30 mm×50 cm, Seikagaku Kogyo, Ltd., Japan) and eluted with 0.1 M NaCl and 0.05 M Tris-HCl buffer solution (pH 7.5). Ammonium sulfate (72 g) was dissolved in the resulting active fraction (300 ml) and to the solution was added the above buffer solution to make the whole volume 360 ml, which was adsorbed on a hydrophobic chromatography column (Butyl toyopearl 650C, inner diameter: 30 mm×50 cm, Toso, Ltd., Japan). The column was subjected to ion-concentration gradient chromatography by using 0.05 M Tris-HCl buffer solution containing ammonium sulfate ranging from 20% to 0%. Active fractions (200 ml) were collected and ammonium sulfate (60 g) was dissolved therein to effect salting out. The salted-out product was centrifuged by a cooling centrifuge under conditions of 5000×g at 5° C. for 20 minutes and subjected to desalting by using a column of Sephadex G-25. The active fraction thus obtained was adsorbed on a column of DEAE cellulofine A-500 (inner diameter: 30 mm×50 cm, Seikakagu Kogyo, Ltd., Japan) and eluted with 0.1 M NaCl and 0.05 M Tris-HCl buffer solution (pH 7.5). The active fraction (250 ml) was subjected to dialysis against 10 l of distilled water at 5° C. The dialyzed solution was freeze-dried with a freeze-drier (FDS-1 Type, Tokyo Rika Kikai, Ltd., Japan) under conditions of 30 Pa to obtain a dry authentic sample of choline oxidase (75 mg).

TABLE 5

| Purification step | Total Activity (U) | Total Protein (mg) | Specific Activity (U/mg) |
| --- | --- | --- | --- |
| Ethanol precipitation | 1,200 | 24,000 | 0.05 |
| Ammonium sulfate salting out | 1,191 | 8,505 | 0.14 |
| Sephadex G-25 (1) | 1,080 | 7,200 | 0.15 |
| DEAE cellulofine (1) | 1,030 | 600 | 1.72 |
| Hydrophobic chromatography (1) | 990 | 250 | 3.96 |
| Sephadex G-25 (2) | 985 | 240 | 4.10 |
| DEAE cellulofine (2) | 975 | 150 | 6.50 |
| Hydrophobic chromatography (2) | 800 | 113 | 7.05 |
| Sephadex G-25 (3) | 710 | 100 | 7.10 |
| DEAE cellulofine (3) | 624 | 80 | 7.80 |
| Dry authentic sample | 585 | 75 | 7.85 |

The total activity, the amount of total protein and the specific activity of choline oxidase in each purification step are shown in the above Table 5.

The method for determining the activity was that described hereinabove. The determination of protein was carried out according to the method for measuring BCA protein (Analyticl Biochemistry, Vol. 150, pp 76-85, 1985). According to the above electrophoresis, the purified authentic sample of enzyme thus obtained showed the band of a single homogenious protein.

EXAMPLE 11

The crude sample of enzyme obtained in Example 7 (350 g) was dissolved in the above buffer solution (4 l) and centrifuged with a cooling centrifuge (CR26H Type, Hitachi Seisakusho, Ltd., Japan) under conditions of 5000×g at 5° C. for 20 minutes to remove insolubles to obtain a supernatant (3940 ml). Ammonium sulfate (2500 g) was slowly dissolved in the supernatant to effect salting out. After standing at 5° C. for 14 hours, the supernatant was centrifuged again with a cooling centrifuge under conditions of 5000×g at 5° C. for 30 minutes. The salted out product was dissolved in the above buffer solution (500 ml), passed through Sephadex G-25 column (inner diameter: 33 mm×50 cm, Pharmacia Labs., Inc., U.S.A.) and eluted with the above buffer solution to effect desalting. The active fraction thus obtained (800 ml) was adsorbed on a column of DEAE cellulofine A-500 (inner diameter: 30 mm×50 cm, Seikagaku Kogyo, Ltd., Japan), washed with the above buffer solution (3 l) and eluted with 0.1 M NaCl and 0.05 M Tris-HCl buffer solution (pH 7.5). Active fractions (500 m±) were collected and ammonium sulfate (120 g) was dissolved therein. To the solution was added the above buffer solution to make the whole volume 600 ml, which was adsorbed on a hydrophobic chromatography column (Butyl toyopearl 650C, inner diameter: 30 mm×50 cm, Toso, Ltd., Japan) The column was subjected to ion-concentration gradient chromatography by using 0.05 M Tris-HCl buffer solution containing ammonium sulfate ranging from 20% to 0%. Active fractions (300 ml) were collected and ammonium sulfate (90 g) was dissolved therein to effect salting out. The salted-out product was separated with a cooling centrifuge under conditions of 5000×g at 5° C. for 20 minutes and subjected desalting by using Sephadex G-25 column. The active fraction thus obtained was adsorbed on a column of DEAE cellulofine A-500 (inner diameter: 30 mm×50 cm, Seikagaku Kogyo, Ltd., Japan)and eluted with 0.1 M NaCl and 0.05 M Tris-HCl buffer solution (pH 7.5). The active fraction (300 ml) was subjected to dialysis against distilled water (10 l) at 5° C. and the dialyzed solution was freeze-dried with a freeze drier (FD-1 Type, Tokyo Rika Kikai, Ltd., Japan) under conditions of 30 Pa to obtain a dry authentic sample of choline oxidase (132 mg). The dry sample had the specific activity of 8.95 U/mg and, according to the above electrophoresis, the sample showed the band of a single homogenous protein.

TABLE 6

| Purification step | Total Activity (U) | Total Protein (mg) | Specific Activity (U/mg) |
| --- | --- | --- | --- |
| Ethanol precipitation | 9,976 | 23,200 | 0.43 |
| Ammonium sulfate salting out | 9,850 | 8,874 | 1.11 |
| Sephadex G-25 (1) | 9,200 | 8,000 | 1.15 |
| DEAE cellulofine (1) | 5,800 | 974 | 5.95 |
| Hydrophobic chromatography | 2,700 | 331 | 8.15 |
| Sephadex G-25 (2) | 2,450 | 285 | 8.59 |
| DEAE cellulofine (2) | 1,340 | 150 | 8.95 |
| Dry authentic sample | 1,180 | 132 | 8.95 |

The total activity, the amount of total protein and the specific activity of choline oxidase in each purification step are shown in the above Table 6.

The method for determining the activity was that described hereinbefore and the determination of protein was carried out according to the method of measuring BCA protein (Analytical Biochemistry, Vol. 150, pp 76-85, 1985).

EXAMPLE 12

Enzymatic properties of the purified authentic enzyme sample of *Thermoactinomyces monosporus* IFO 14050 obtained in Example 10 (hereinafter referred to as authentic sample T) and the purified authentic enzyme sample of *Saccharopolyspora hirsuta* ATCC 27876 obtained in Example 11 (hereinafter referred to as authentic sample S) were evaluated.

(1) Substrate specificity

According to the same manner as the above method for determining enzymatic activity, enzymatic activities were determined with respect to choline, betaine aldehyde, N-methylaminoethanol, dimethylaminoethanol, monoethanolamine, diethanolamine and triethanolamine. As the results, the enzymes showed reactivity to choline, betaine aldehyde and dimethylaminoethanol and almost the same results as those in Table 2 were obtained.

(2) Optimal pH

According to the same manner as that described hereinabove, optimal pH's of the authentic samples T and S were determined by using a citric acid-dipotassium hydrogen phosphate buffer solution (pH 4-7), a phosphoric acid-potassium hydroxide buffer solution (pH 6-8), a Tris-HCl buffer solution (pH 7-9), glycine-sodium hydroxide (pH 9-11) and boric acid-sodium carbonate (pH 9-10).

Figure 10:
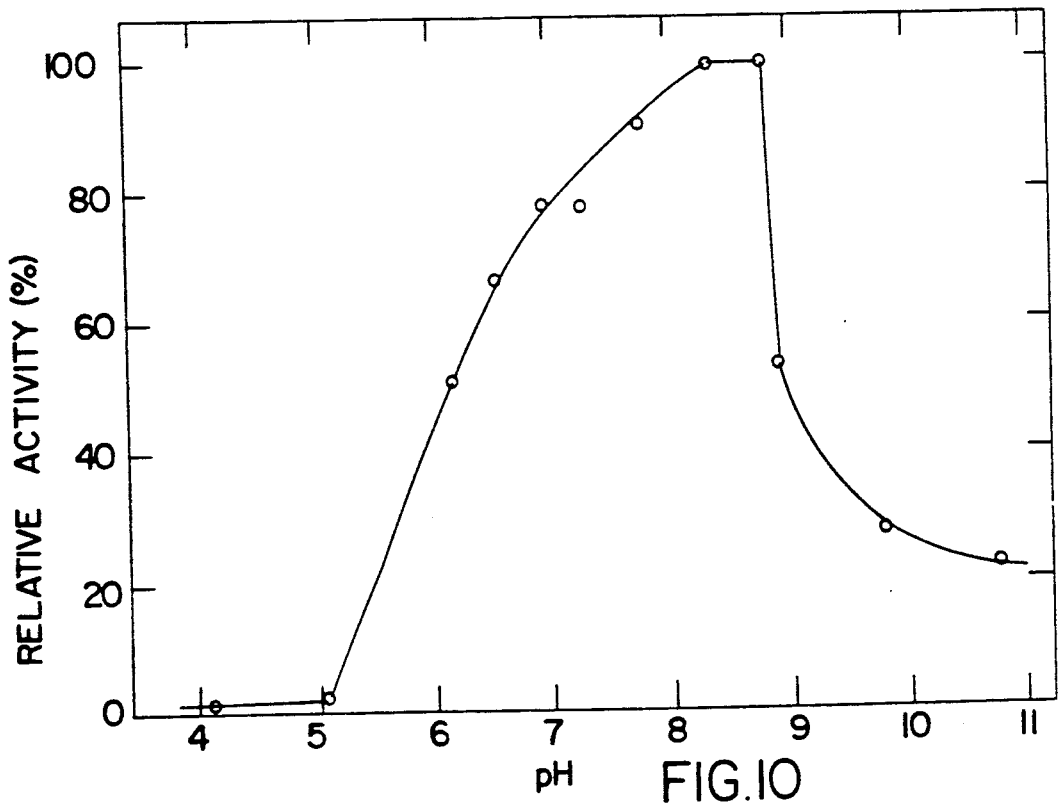
FIGS. 10 and 11 are graphs illustrating optimal pH's of enzymes obtained in Examples 10 (authentic sample T) and 11 (authentic sample S) hereinafter, respectively.
Figure 11:
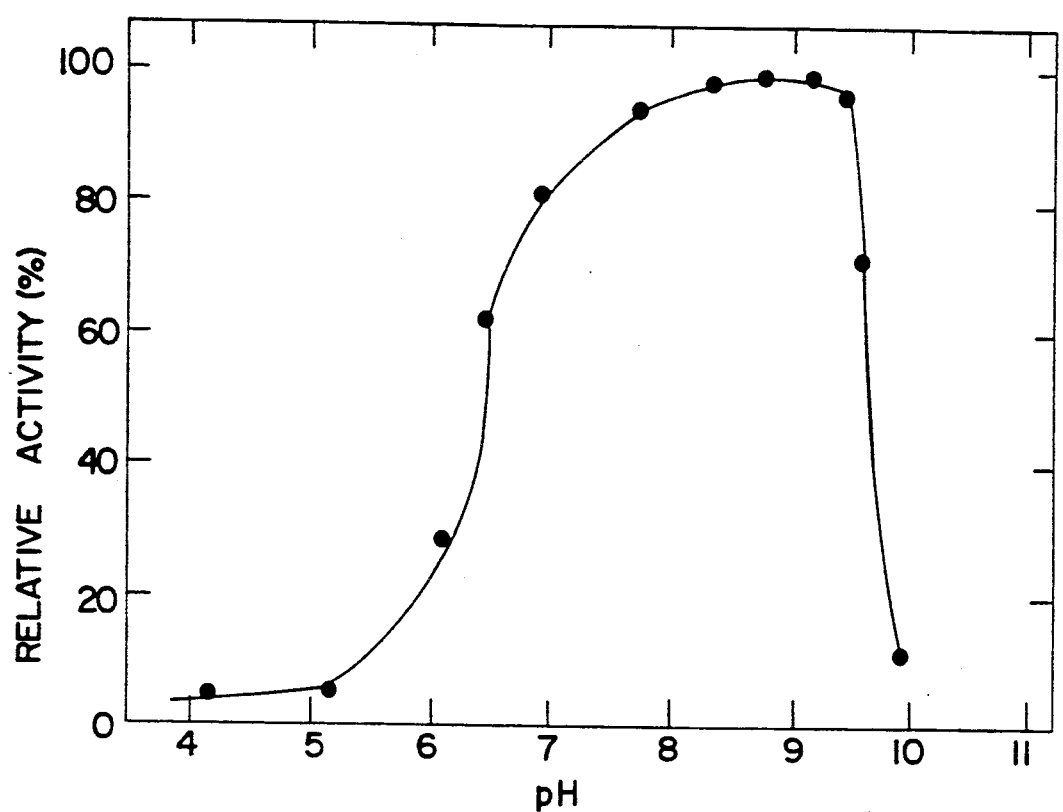

The results of the authentic sample T is shown in FIG. 10 and the results of the authentic sample S is shown in FIG. 11.

(3) pH stability

According to the same manner as that described hereinabove, pH stabilities of the authentic samples T and S were determined by using a citric acid-dipotassium hydrogen phosphate buffer solution (pH 4-7), a phosphorid acid-potassium hydroxide buffer solution (pH 6-8), a Tris-HCl buffer solution (pH 7-9), glycine-sodium hydroxide (pH 9-11) and boric acid-sodium carbonate (pH 9-10).

Figure 12:
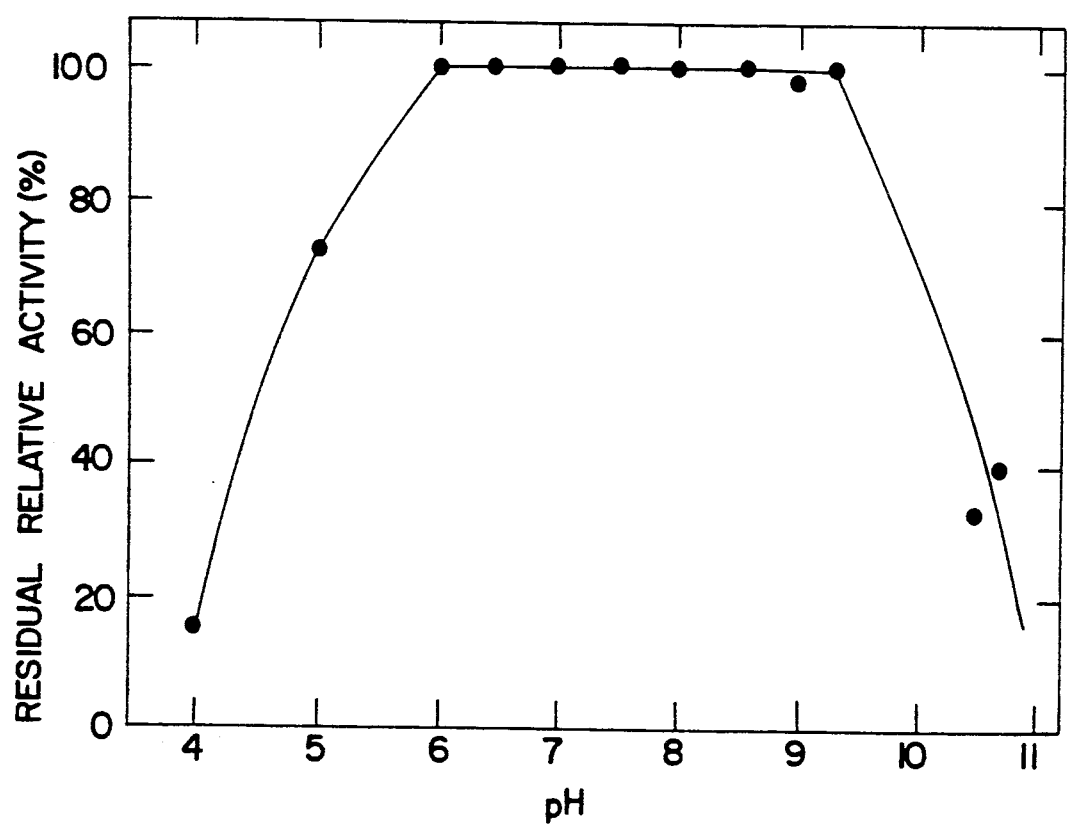
FIGS. 12 and 13 are graphs illustrating pH stabilities of the authentic samples T and S, respectively.
Figure 13:
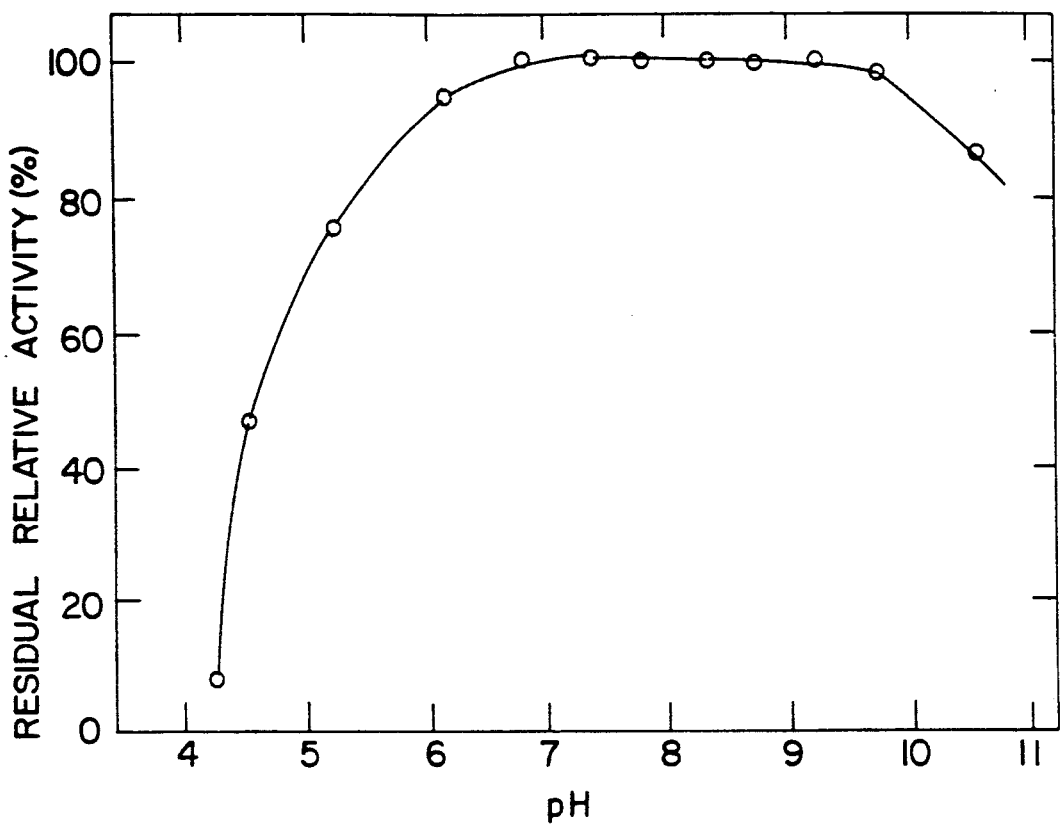

The results of the authentic sample T is shown in FIG. 12 and the results of the authentic sample S is shown in FIG. 13.

(4) Optimal temperature

According to the same manner as that described hereinabove, optimal temperatures were determined.

Figure 14:
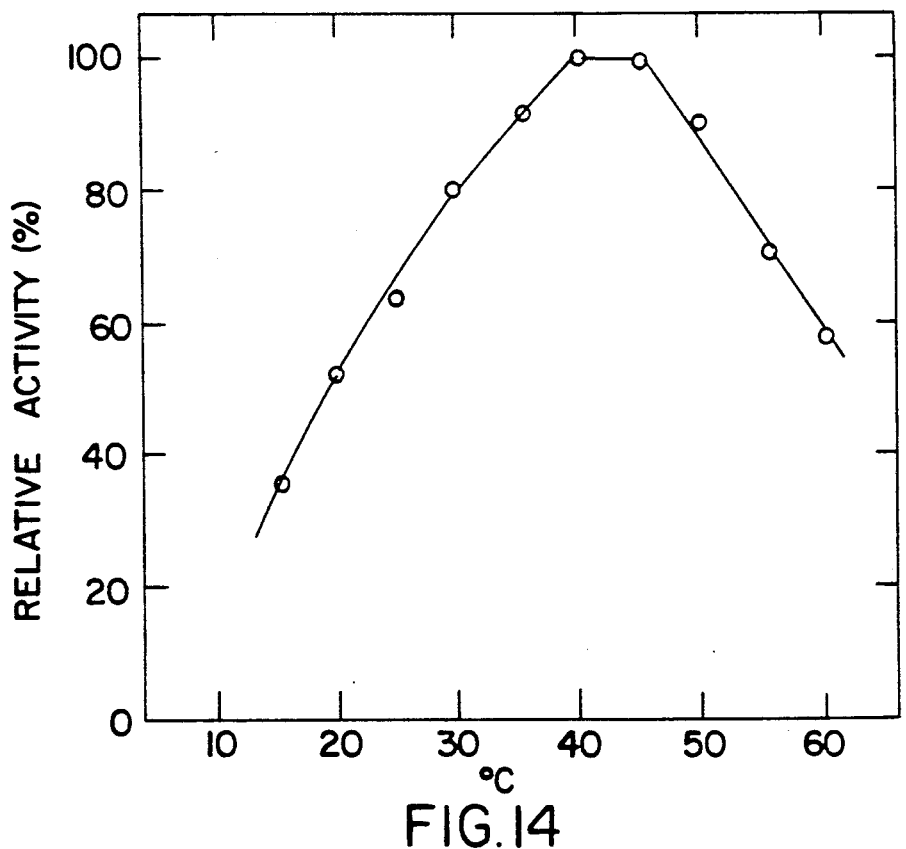
FIGS. 14 and 15 are graphs illustrating optimal temperatures of authentic samples T and S, respectively.
Figure 15:
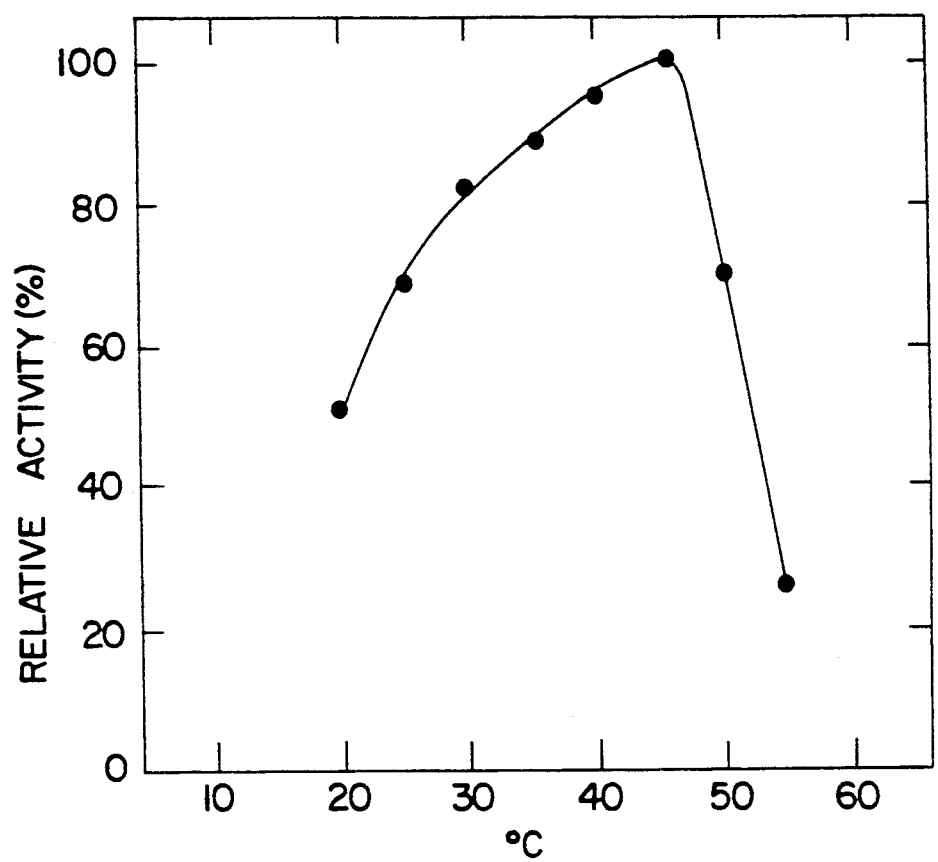

The results of the authentic sample T is shown in FIG. 14 and the results of the authentic sample S is shown in FIG. 15.

(5) Thermostability 0.05 M Tris-HCl buffer solution (pH 7.5) containing the authentic sample T or S (0.5 U/ ml) was heated at various temperature and the residual enzymatic activity was determined. The results of the authentic sample T were agreed to those of the crude sample of Example 5 in FIG. 4 (symbol ○). The results of the authentic sample S were agreed to those of FIG. 9.

(6) Inhibitors

According to the same manner as that described hereinabove, the inhibitory effects of the metal salts as shown in Table 3 were examined. Both authentic samples T and S showed almost the same results as those shown in Table 3.

(7) Measurement of molecular weight

The molecular weights of the enzymes were determined according to the above method (9) (a).

Namely, the molecular weights of the enzymes were determined by molecular sieve high performance liquid chromatography under the following conditions:

column: TSK gel ® G 3000 SW (inner diameter: 7.5 mm ×60 cm, Toso, Ltd., Japan)

apparatus: Computer Control Excellent Pump CCPE type, UV-8000 type detector, Toso, Ltd. Japan developing agent: 50 mM potassium sodium phosphate buffer solution (pH 7.0) and 0.2 M NaCl flow rate: 0.5 ml/min. ["High Performance Liquid Chromatography of Proteins, Peptides", pp 203-213 ("Kagaku", extra number 102, 1984)].

The retention time was 41.4 minutes. By using yeast glutamate dehydrogenase (molecular weight: 290 K), swine cardiac muscle lactate dehydrogenase (molecular weight: 142 K), yeast enolase (molecular weight: 67 K), yeast adenylate kinase (molecular weight: 32 K) and equine cardiac muscle cytochrome C (molecular weight: 12.4 K) as standard samples, the molecular weights of the enzymes were determined. As the results, the molecular weight of the authentic sample T was about 64,000 and that of the authentic sample S was about 93,000.

Then, the molecular weights of the enzymes were determined according to the above method (9) (c).

Namely, the molecular weights of the enzymes were determined according to the polyacrylamide electrophoresis of a system of discontinuous buffer solutions described in "Nature", Vol. 227, p 680 (1970). The sample was treated in a solution containing a 0.0625 M Tris-HCl buffer solution (pH 6.8), 2% SDS, 10% glycerol and 5% mercaptoethanol at 100° C. for 5 minutes. Then, electrophoresis was conducted by using SDS-PAG plate 10/20 (84×90×1.0 mm, manufactured by Daiichi Kagaku Yakuhin Ltd., Japan) and a solution containing 0.025 M Tris, 0.1% SDS and 0.192 M glycine as the electrophoresis buffer solution (pH 8.4) under conditions of the current of 60 mA for 60 minutes. As the standard samples, phosphorylase b (molecular weight: 94000), bovine serum albumin (molecular weigh: 67000), ovalbumin (molecular weight: 43000), carbonic anhydrase (molecular weight 30000), trypsin inhibitor (molecular weight: 20100) and α-lactalbumin (molecular weight: 14400) were used. The molecular weights of both authentic samples T and S were determined to be $6 \times 10^4$, respectively.

(8) Isoelectric point

Isoelectric point electorphoresis was carried out by using amphorine polyacrylamide gel plate (pH 4.0-6.5). The isoelectric point of the authentic sample T was about 4.8 and that of authentic sample S was about 5.5.

(9) Electrophoresis

The enzymes were treated with a solution composed of a 0.0625 M Tris-HCl buffer solution (pH 6.8) and 15% glycerol and subjected to electrophoresis by using a concentration gradient acrylamide gel, PAG plate 4/15 (84×90×1.0 mm, Daiichi Kagaku Yakuhin, Ltd., Japan) and a solution (pH 8.4) composed of 0.025 M Tris and 0.192 M glycine as the buffer solution for electrophoresis under conditions of a current of 30 mA for 60 minutes. Both authentic samples T and S showed single bands.

As described hereinabove, the choline oxidase of the present invention has superior thermal stability in comparison with conventional choline oxidase and is useful for practical use in the fields of chemical analyses and clinical tests.

What is claimed is:

1. A novel purified choline oxidase being thermostable at 50° C. at pH 7 to 9 without any loss of residual enzymatic activity, having optimal pH within the range of 7.5 to 9 and optimal temperature within the range of about 40° to 55° C. and its stable pH range of 7 to 9 and an isoelectric point within the range of 4.5 to 5.5.

2. The choline oxidase according to claim 1, wherein the molecular weight thereof is 50,000 to 95,000 in the case of determination by gel filtration method, or $5.5 \times 10^4$ to $6.5 \times 10^4$ in the case of determination by SDS method.

* * * * *